United States Patent [19]

Xiong et al.

[11] Patent Number: 5,766,602

[45] Date of Patent: Jun. 16, 1998

[54] RECOMBINANT PACKAGING DEFECTIVE SINDBIS VIRUS VACCINES

[75] Inventors: Cheng Xiong; Robert B. Grieve, both of Ft. Collins, Colo.

[73] Assignee: Heska Corporation, Fort Collins, Colo.

[21] Appl. No.: 375,235

[22] Filed: Jan. 19, 1995

Related U.S. Application Data

[63] Continuation of Ser. No. 15,414, Feb. 8, 1993.

[51] Int. Cl.[6] .......................... A61K 39/12; C12P 21/00; C12N 7/01; C12N 15/00
[52] U.S. Cl. ............................... 424/218.1; 424/199.1; 435/320.1; 435/69.3; 435/235.1
[58] Field of Search .......................... 424/199.1, 218.1; 435/69.3, 235.1, 320.1

[56] References Cited

U.S. PATENT DOCUMENTS

| | | | |
|---|---|---|---|
| 4,391,822 | 7/1983 | Frenkel et al. | 424/283 |
| 4,473,548 | 9/1984 | Frenkel et al. | 424/88 |
| 4,473,549 | 9/1984 | Frenkel et al. | 424/88 |
| 4,564,592 | 1/1986 | Gaafar et al. | 435/68 |
| 5,045,313 | 9/1991 | Frenkel et al. | 424/88 |

FOREIGN PATENT DOCUMENTS

| | | |
|---|---|---|
| 2031811 | 6/1991 | Canada. |
| 0 391 319 A1 | 10/1990 | European Pat. Off.. |
| WO 88/09372 | 12/1988 | WIPO. |
| WO 89/12683 | 12/1989 | WIPO. |
| WO 92/11366 | 7/1992 | WIPO. |

OTHER PUBLICATIONS

Araujo et al., "Partially Purified Antigen Preparations of Toxoplasma gondii Protect Against Lethal Infection in Mice", pp. 122–126, 1984, *Infect. Immun.*, vol. 45, No. 1 (Jul.).

Bredenbeek et al., "Animal RNA Virus Expression Systems", pp. 297–310, 1992, *Seminars in Virology*, vol. 3.

Bülow et al., "Protection of Mice from Fatal Toxoplasma gondii infection by Immunization with P30 Antigen in Liposomes", pp. 3496–3500, 1991, *J. Immunol.*, vol. 147, No. 10 (Nov. 15).

Burg et al., "Molecular Analysis of the Gene Encoding the Major Surface Antigen of Toxoplasma gondii", pp. 3584–3591, 1988, *J. Immunol.*, vol. 141, No. 10 (Nov. 15).

Cesbron–Delauw et al., "Molecular Characterization of a 23–Kilodalton Major Antigen Secreted by Xoxoplasma gondii", pp. 7537–7541, 1989, *Proc. Natl. Acad. Sci. USA*, vol. 86, Oct.

Dougan et al., "Live Bacterial Vaccines and Their Application as Carriers for Foreign Antigens", pp. 271–300, 1989, in *Advances in Veterinary Science and Comparative Medicine*, vol. 33, Academic Press, Inc.

Esposito et al., "Infectious Recombinant Vectored Virus Vaccines", pp. 195–247, 1989, in *Advances in Science and Comparative Medicine*, vol. 33.

Faragher et al., "Genome Sequences of a Mouse–Avirulent and a Mouse–Virulent Strain of Ross River Virus", pp. 509–526, 1988, *Virol.*, vol. 163.

Geigenmüller–Gnirke et al., "Complementation between Sindbis Viral RNAs Produces Infectious Particles with a Bipartite Genome", pp. 3253–3257, 1991, *Proc. Natl. Acad. Sci. USA*, vol. 88, Apr.

Hertz et al., "Utilization of Heterologous Alphavirus Junction Sequences as Promoters by Sindbis Virus", pp. 857–864, 1992, *J. Virol.*, vol. 66, No. 2 (Feb.).

Huang et al., "Infection Initiated by the RNA Pregenome of a DNA Virus", pp. 5435–5439, 1991, *J. Virol.*, vol. 65, No. 10 (Oct.).

Huang et al., "RNA Viruses as Gene Expression Vectors", pp. 85–91, 1989, *Virus Genes*, vol. 3, No. 1.

Johnson et al., "Cloning, Expression and Nucleotide Sequence of the Gene Fragment Encoding an Antigenic Portion of the Nucleoside Triphosphate Hydrolase of *Toxoplasma gondii*", pp. 215–220, 1989, *Gene*, vol. 85.

Johnson et al., "Monoclonal Antibodies to Toxoplasma Cell Membrane Surface Antigens Protect Mice from Toxoplasmosis", pp. 351–356, 1983, *J. Protozool.*, vol. 30, No. 2 (May).

Kasper et al., "An Unexpected Response to Vaccination with a Purified Major Membrane Tachyzoite Antigen (P30) of *Toxoplasma gondii*", pp. 3426–3530, 1985, *J. Immunol.*, vol. 134, No. 5 (May).

Kasper et al., "Identification of Stage–Specific Sporozoite Antigens of *Toxoplasma gondii* by Monoclonal Antibodies", pp. 443–449, 1984, *J. Immunol.*, vol. 132, No. 1 (Jan.).

Kasper, "Isolation and Characterization of a Monoclonal Anti–P30 Antibody Resistant Mutant of *Toxoplasma gondii*", pp. 433–445, 1987, *Para. Immunol.*, vol. 9.

Kasper et al., "Purification of a Major Membrane Protein of *Toxoplasma gondii* by Immunoabsorption with a Monoclonal Antibody", pp. 2407–2412, 1983, *J. Immunol.*, vol. 130, No. 5 (May).

(List continued on next page.)

*Primary Examiner*—Ponnathapura Achutamurthy
*Assistant Examiner*—Phuong T. Bui

[57] ABSTRACT

The present invention is directed toward a recombinant virus particle vaccine comprising a recombinant molecule packaged in an alphavirus coat. A preferred recombinant molecule of the present invention comprises a nucleic acid sequence that encodes a protective compound (e.g. a protective protein or a protective RNA) capable of protecting an animal from a disease, such that the nucleic acid sequence is operatively linked to a packaging-defective alphavirus expression vector that is capable of directing replication and transcription of the recombinant molecule. The invention also includes methods to produce and use such vaccines to protect animals from disease, particularly from disease caused by protozoan parasites such as *Toxoplasma gondii*, helminth parasites, ectoparasites, fungi, bacteria, or viruses.

57 Claims, 6 Drawing Sheets

OTHER PUBLICATIONS

Khan et al., "A Purified Parasite Antigen (P30) Mediates CD8+ T Cell Immunity Against Fatal *Toxoplasma gondii* Infection in Mice", pp. 3501–3506, 1991, *J. Immunol.*, vol. 147, No. 10 (Nov. 15).

Khan et al., "Induction of Antigen–Specific Parasiticidal Cytotoxic T Cell Splenocytes by a Major Membrane Protein (P30) of *Toxoplasma gondii*", pp. 3600–3605, 1988, *J. Immunol.*, vol. 141, No. 10 (Nov. 15).

Khan et al., "Production of γ Interferon by Cultured Human Lymphocytes Stimulated with a Purified Membrane Protein (P30) from *Toxoplasma gondii*", pp. 979–984, 1988, *J. Infect. Dis.*, vol. 157, No. 5 (May).

Levis et al., "Deletion Mapping of Sindbis Virus DI RNAs Derived from cDNAs Defines the Sequences Essential for Replication and Packaging", pp. 137–145, 1986, *Cell*, vol. 44 (Jan. 17).

Levis et al., "Engineered Defective Interfering RNAs of Sindbis Virus Express Bacterial Chloramphenicol Acetyltransferase in Avian Cells", pp. 4811–4815, 1987, *Proc. Natl. Acad. Sci. USA* vol. 84. Jul.

Levis et al., "Promoter for Sindbis Virus RNA–Dependent Subgenomic RNA Transcription", pp. 1726–1733, 1990, *J. Virol.*, vol. 64, No. 4 (Apr.).

Li et al., "Rescue of Sindbis Virus–Specific RNA Replication and Transcription by Using a Vaccinia Virus Recombinant", pp. 6714–6723, 1991, *J. Virol.*, vol. 65, No. 12 (Dec.).

Liljeström et al., "A New Generation of Animal Cell Expression Vectors Based on the Semliki Forest Virus Replicon", 1991, *Bio/Technology*. vol. 9, Dec. pp. 1356–1361.

Liljeström et al., "In Vitro Mutagenesis of a Full–Length cDNA Clone of Semliki Forest Virus: the Small 6,000–Molecular–Weight Membrane Protein Modulates Virus Release", pp. 4107–4113, 1991, *J. Virol.*, vol. 65, No. 8 (Aug.).

London et al., "Infectious Enveloped RNA Virus Antigenic Chimeras", pp. 207–211, 1992, *Proc. Natl. Acad. Sci. USA*, vol. 89, Jan.

Makioka et al., "Toxoplasmacidal Activity of Macrophages Activated by Recombinant Major Surface Antigen (P30) of *Toxoplasma gondii*", pp. 2851–2852, 1991, *Infect. Immun.*, vol. 59, No. 8 (Aug.).

Mann et al., "Construction of a Retrovirus Packaging Mutant and Its Use to Produce Helper–Free Defective Retrovirus", pp. 153–159, 1983, *Cell*, vol. 33, May.

Melton et al., "Efficient in vitro Synthesis of Biologically Active RNA and RNA Hybridization Probes from Plasmids Containing a Bacteriophage SP6 Promoter", pp. 7035–7056, 1984, *Nucleic Acids Res.*, vol. 12, No. 18.

Nagel et al., "The Major Surface Antigen, P30, of *Toxoplasma gondii* is Anchored by a Glycolipid", pp. 5569–5574, 1989, *J. Biol. Chem.*, vol. 264, No. 10 (Apr. 5).

Ou et al., "Sequence Studies of Several Alphavirus Genomic RNAs in the Region Containing the Start of the Subgenomic RNA", pp. 5235–5239, 1982, *Proc. Natl. Acad. Sci. USA*, vol. 79, Sep.

Packer et al., "Murine Immune Responses to Recombinant *Toxoplasma gondii* Antigens", pp. 402–409, 1991 *J. Parasitol.*, vol. 77, No. 3.

Partanen et al., "Immunoblot Analysis of *Toxoplasma gondii* Antigens by Human Immunoglobulins G, M, and A Antibodies at Different Stages of Infection", pp. 133–135, 1984, *J. Clin. Microbiol.*, vol. 20, No. 1 (Jul.).

Potasman et al., "Analysis of *Toxoplasma gondii* Antigens Recognized by Human Sera Obtained Before and After Acute Infection", pp. 650–657, 1986, *J. Infect. Dis.*, vol. 154, No. 4 (Oct.).

Prince et al., "Cloning, Expression and cDNA Sequence of Surface Antigen P22 from *Toxoplasma gondii*", pp. 97–106, 1990, *Mol. Biochem. Parasitol.*, vol. 43.

Prince et al., Cloning of cDNAs Encoding a 28 Kilodalton Antigen of *Toxoplasma gondii*, pp. 3–14, 1989, *Mol. Biochem. Parasitol.*, vol. 34.

Raju et al., "Analysis of Sindbis Virus Promoter Recognition in vivo, Using Novel Vectors with Two Subgenomic mRNA Promoters", pp. 2501–2510, 1991, *J. Virol.*, vol. 65, No. 5 (May).

Rice et al., "Production of Infectious RNA Transcripts from Sindbis Virus cDNA Clones: Mapping of Lethal Mutations, Rescue of a Temperature–Sensitive Marker, and in vitro Mutagenesis to Generate Defined Mutants", pp. 3809–3819, 1987, *J. Virol.*, vol. 61, No. 12 (Dec.).

Rice et al., "Synthesis, Cleavage and Sequence Analysis of DNA Complementary to the 26 S Messenger RNA of Sindbis Virus", pp. 315–340, 1981, *J. Mol. Biol.*, vol. 150.

Rodriguez et al., "Major Surface Protein of *Toxoplasma gondii* (P30) Contains an Immunodominant Region with Repetitive Epitopes", pp. 747–749, 1985 *Eur. J. Immunol.*, vol. 15.

Saavedra et al., "Human T Cell Clone Identifies a Potentially Protective 54–kDa Protein Antigen of *Toxoplasma gondii* Cloned and Expressed in *Escherichia coli*", pp. 1975–1982, 1991, *J. Immunol.*, vol. 147, No. 6 (Sep. 15).

Santoro et al., "Serodiagnosis of Toxoplasma Infection Using a Purified Parasite Protein (P30)", pp. 262–269, 1985 *Clin. exp. Immunol.*, vol. 62.

Sharma et al., "Western Blot Analysis of the Antigens of *Toxoplasma gondii* Recognized by Human IgM and IgG Antibodies", pp. 977–983, 1983, *J. Immunol.*, vol. 131, No. 2 (Aug.).

Smith et al., "Single–Step Purification of Polypeptides Expressed in *Escherichia coli* as Fusions with Glutathione S–Transferase", pp. 31–40, 1988, *Gene*, vol. 67.

Strauss et al., "Complete Nucleotide Sequence of the Genomic RNA of Sindbis Virus", pp. 92–110, 1984 *Virol.*, vol. 133.

Strauss et al., "Structure and Replication of the Alphavirus Genome", pp. 35–90, Chapter 3, 1986, in *The Togaviridae and Flaviviridae*, (Schlesinger and Schlesinger, eds.).

Ware et al., "Strain–Specific Antigens of *Toxoplasma gondii*", pp. 778–783, 1987, *Inf. Immun.*, vol. 55, No. 3 (Mar.).

Weiss et al., "Evidence for Specificity in the Encapsidation of Sindbis Virus RNAs", pp. 5310–5318, 1989, *J. Virol.*, vol. 63, No. 12 (Dec.).

Xiong et al., "Sindbis Virus: An Efficient, Broad Host Range Vector for Gene Expression in Animal Cells", pp. 1188–1191, 1989, *Science*, vol. 243, Mar. (Reprint Series).

Fox "No Winner Against AIDS" Bio/Techology vol. 12, Feb. 1994, p. 128.

Ellis, R.W. 1988 "New Technologies for Making Vaccines", In: Vaccines, S. Plotkin & E. Mortimer Eds. W.B. Saunders Co. pp. 568–575.

FIG. I
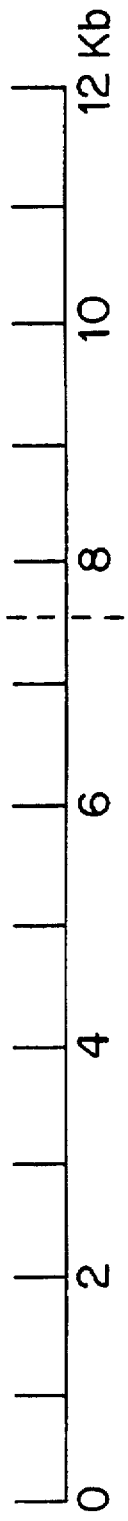
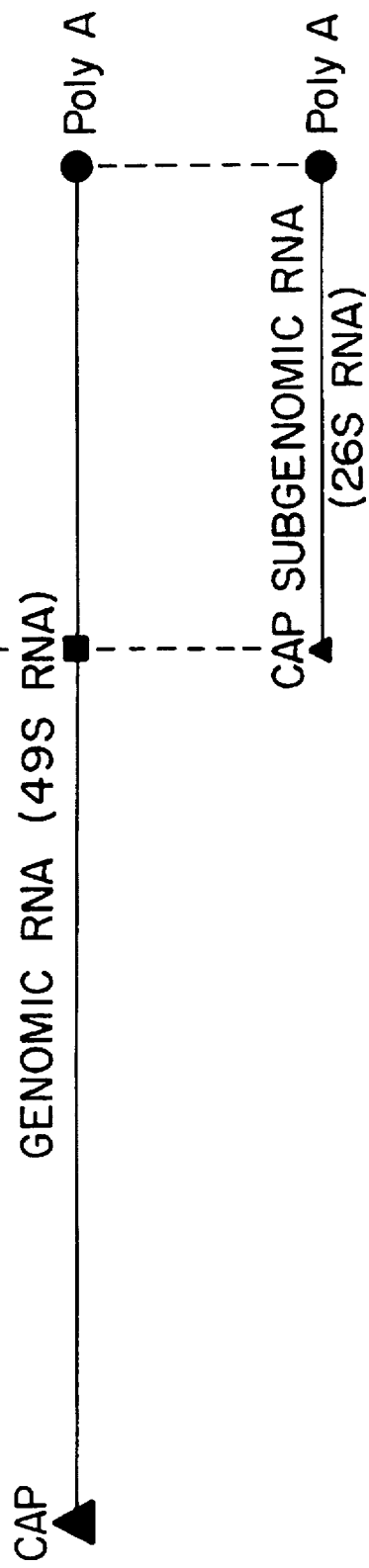

FIG. 3

PREDICTED CODING REGION OF P30 GENE: ATG — TGA nP30.1008: ATG — Xbal — TGA — Xhol nP30.873: ATG — Xbal — TGA — Xhol nP30.924: Xbal — TGA — Xhol nP30.789: ATG — Xbal — TGA — Xhol nP30.867SS: ATG — Xbal — SS — TGA — Xhol nP30.924SS: ATG — Xbal — SS — TGA — Xhol nP30.783SS: ATG — Xbal — SS — TGA — Xhol

SS = SIGNAL SEGMENT 5,766,602

SEQUENCE LISTING ( 1 ) GENERAL INFORMATION:

( i i i ) NUMBER OF SEQUENCES: 10

( 2 ) INFORMATION FOR SEQ ID NO:1:

( i ) SEQUENCE CHARACTERISTICS:
        ( A ) LENGTH: 1011 base pairs
        ( B ) TYPE: nucleic acid
        ( C ) STRANDEDNESS: single
        ( D ) TOPOLOGY: linear (i i) MOLECULE TYPE: cDNA (i x) FEATURE:
  (A) NAME/KEY: CDS
  (B) LOCATION: 1..1011

(x i) SEQUENCE DESCRIPTION: SEQ ID NO:1:

| ATG | TCG | GTT | TCG | CTG | CAC | CAC | TTC | ATT | ATT | TCT | TCT | GGT | TTT | TTG | ACG | 48 |
| Met | Ser | Val | Ser | Leu | His | His | Phe | Ile | Ile | Ser | Ser | Gly | Phe | Leu | Thr | |
| 1 | | | | 5 | | | | | 10 | | | | | 15 | | |

| AGT | ATG | TTT | CCG | AAG | GCA | GTG | AGA | CGC | GCC | GTC | ACG | GCA | GGG | GTG | TTT | 96 |
| Ser | Met | Phe | Pro | Lys | Ala | Val | Arg | Arg | Ala | Val | Thr | Ala | Gly | Val | Phe | |
| | | | 20 | | | | | 25 | | | | | 30 | | | |

| GCC | GCG | CCC | ACA | CTG | ATG | TCG | TTC | TTG | CGA | TGT | GGC | GTT | ATG | GCA | TCG | 144 |
| Ala | Ala | Pro | Thr | Leu | Met | Ser | Phe | Leu | Arg | Cys | Gly | Val | Met | Ala | Ser | |
| | | 35 | | | | | 40 | | | | | 45 | | | | |

| GAT | CCC | CCT | CTT | GTT | GCC | AAT | CAA | GTT | GTC | ACC | TGC | CCA | GAT | AAA | AAA | 192 |
| Asp | Pro | Pro | Leu | Val | Ala | Asn | Gln | Val | Val | Thr | Cys | Pro | Asp | Lys | Lys | |
| | 50 | | | | | 55 | | | | | 60 | | | | | |

| TCG | ACA | GCC | GCG | GTC | ATT | CTC | ACA | CCG | ACG | GAG | AAC | CAC | TTC | ACT | CTC | 240 |
| Ser | Thr | Ala | Ala | Val | Ile | Leu | Thr | Pro | Thr | Glu | Asn | His | Phe | Thr | Leu | |
| 65 | | | | 70 | | | | | 75 | | | | | 80 | | |

| AAG | TGC | CCT | AAA | ACA | GCG | CTC | ACA | GAG | CCT | CCC | ACT | CTT | GCG | TAC | TCA | 288 |
| Lys | Cys | Pro | Lys | Thr | Ala | Leu | Thr | Glu | Pro | Pro | Thr | Leu | Ala | Tyr | Ser | |
| | | | | 85 | | | | | 90 | | | | | 95 | | |

| CCC | AAC | AGG | CAA | ATC | TGC | CCA | GCG | GGT | ACT | ACA | AGT | AGC | TGT | ACA | TCA | 336 |
| Pro | Asn | Arg | Gln | Ile | Cys | Pro | Ala | Gly | Thr | Thr | Ser | Ser | Cys | Thr | Ser | |
| | | | 100 | | | | | 105 | | | | | 110 | | | |

| AAG | GCT | GTA | ACA | TTG | AGC | TCC | TTG | ATT | CCT | GAA | GCA | GAA | GAT | AGC | TGG | 384 |
| Lys | Ala | Val | Thr | Leu | Ser | Ser | Leu | Ile | Pro | Glu | Ala | Glu | Asp | Ser | Trp | |
| | | | 115 | | | | | 120 | | | | | 125 | | | |

| TGG | ACG | GGG | GAT | TCT | GCT | AGT | CTC | GAC | ACG | GCA | GGC | ATC | AAA | CTC | ACA | 432 |
| Trp | Thr | Gly | Asp | Ser | Ala | Ser | Leu | Asp | Thr | Ala | Gly | Ile | Lys | Leu | Thr | |
| | | 130 | | | | | 135 | | | | | 140 | | | | |

| GTT | CCA | ATC | GAG | AAG | TTC | CCC | GTG | ACA | ACG | CAG | ACG | TTT | GTG | GTC | GGT | 480 |
| Val | Pro | Ile | Glu | Lys | Phe | Pro | Val | Thr | Thr | Gln | Thr | Phe | Val | Val | Gly | |
| 145 | | | | | 150 | | | | | 155 | | | | | 160 | |

| TGC | ATC | AAG | GGA | GAC | GAC | GCA | CAG | AGT | TGT | ATG | GTC | ACG | GTG | ACA | GTA | 528 |
| Cys | Ile | Lys | Gly | Asp | Asp | Ala | Gln | Ser | Cys | Met | Val | Thr | Val | Thr | Val | |
| | | | | 165 | | | | | 170 | | | | | 175 | | |

| CAA | GCC | AGA | GCC | TCA | TCG | GTC | GTC | AAT | AAT | GTC | GCA | AGG | TGC | TCC | TAC | 576 |
| Gln | Ala | Arg | Ala | Ser | Ser | Val | Val | Asn | Asn | Val | Ala | Arg | Cys | Ser | Tyr | |
| | | | 180 | | | | | 185 | | | | | 190 | | | |

| GGT | GCA | GAC | AGC | ACT | CTT | GGT | CCT | GTC | AAT | TTG | TCT | GCG | GAA | GGA | CCC | 624 |
| Gly | Ala | Asp | Ser | Thr | Leu | Gly | Pro | Val | Asn | Leu | Ser | Ala | Glu | Gly | Pro | |
| | | 195 | | | | | 200 | | | | | 205 | | | | |

| ACT | ACA | ATG | ACC | CTC | GTG | TGC | GGG | AAA | GAT | GGA | GTC | AAA | GTT | CCT | CAA | 672 |
| Thr | Thr | Met | Thr | Leu | Val | Cys | Gly | Lys | Asp | Gly | Val | Lys | Val | Pro | Gln | |
| | 210 | | | | | 215 | | | | | 220 | | | | | |

| GAC | AAC | AAT | CAG | TAC | TGT | TCC | GGG | ACG | ACG | CTG | ACT | GGT | TGC | AAC | GAG | 720 |
| Asp | Asn | Asn | Gln | Tyr | Cys | Ser | Gly | Thr | Thr | Leu | Thr | Gly | Cys | Asn | Glu | |
| 225 | | | | | 230 | | | | | 235 | | | | | 240 | |

| AAA | TCG | TTC | AAA | GAT | ATT | TTG | CCA | AAA | TTA | ACT | GAG | AAC | CCG | TGG | CAG | 768 |
| Lys | Ser | Phe | Lys | Asp | Ile | Leu | Pro | Lys | Leu | Thr | Glu | Asn | Pro | Trp | Gln | |
| | | | | 245 | | | | | 250 | | | | | 255 | | |

| GGT | AAC | GCT | TCG | AGT | GAT | AAG | GGT | GCC | ACG | CTA | ACG | ATC | AAG | AAG | GAA | 816 |
| Gly | Asn | Ala | Ser | Ser | Asp | Lys | Gly | Ala | Thr | Leu | Thr | Ile | Lys | Lys | Glu | |
| | | | 260 | | | | | 265 | | | | | 270 | | | |

| GCA | TTT | CCA | GCC | GAG | TCA | AAA | AGC | GTC | ATT | ATT | GGA | TGC | ACA | GGG | GGA | 864 |
| Ala | Phe | Pro | Ala | Glu | Ser | Lys | Ser | Val | Ile | Ile | Gly | Cys | Thr | Gly | Gly | |
| | | 275 | | | | | 280 | | | | | 285 | | | | |

-continued

| | | | | | | | | | | | | | | | | |
|---|---|---|---|---|---|---|---|---|---|---|---|---|---|---|---|---|
| TCG | CCT | GAG | AAG | CAT | CAC | TGT | ACC | GTG | AAA | CTG | GAG | TTT | GCC | GGG | GCT | 912 |
| Ser | Pro | Glu | Lys | His | His | Cys | Thr | Val | Lys | Leu | Glu | Phe | Ala | Gly | Ala | |
| | 290 | | | | | 295 | | | | 300 | | | | | | |
| GCA | GGG | TCA | GCA | AAA | TCG | GCT | GCG | GGA | ACA | GCC | AGT | CAC | GTT | TCC | ATT | 960 |
| Ala | Gly | Ser | Ala | Lys | Ser | Ala | Ala | Gly | Thr | Ala | Ser | His | Val | Ser | Ile | |
| 305 | | | | | 310 | | | | | 315 | | | | | 320 | |
| TTT | GCC | ATG | GTG | ATC | GGA | CTT | ATT | GGC | TCT | ATC | GCA | GCT | TGT | GTC | GCG | 1008 |
| Phe | Ala | Met | Val | Ile | Gly | Leu | Ile | Gly | Ser | Ile | Ala | Ala | Cys | Val | Ala | |
| | | | | 325 | | | | | 330 | | | | | 335 | | |

TGA 1011

( 2 ) INFORMATION FOR SEQ ID NO:2:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Toxoplasma gondii
        ( C ) INDIVIDUAL ISOLATE: P30 antigen gene ( v i i ) IMMEDIATE SOURCE:
        ( B ) CLONE: Primer #1

( i x ) FEATURE:
        ( A ) NAME/KEY: 5'UTR
        ( B ) LOCATION: 1..12

( i x ) FEATURE:
        ( A ) NAME/KEY: CDS
        ( B ) LOCATION: 13..33

( x i ) SEQUENCE DESCRIPTION: SEQ ID NO:2:

CCCGGGTCTA GAATGTCGGT TTCGCTGCAC CAC 33

( 2 ) INFORMATION FOR SEQ ID NO:3:

( i ) SEQUENCE CHARACTERISTICS:
        ( A ) LENGTH: 33 base pairs
        ( B ) TYPE: nucleic acid
        ( C ) STRANDEDNESS: single
        ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
        ( A ) ORGANISM: Toxoplasma gondii
        ( C ) INDIVIDUAL ISOLATE: P30 antigen gene ( v i i ) IMMEDIATE SOURCE:
        ( B ) CLONE: Primer #2

( i x ) FEATURE:
        ( A ) NAME/KEY: 3'UTR
        ( B ) LOCATION: complement (1..17)

( i x ) FEATURE:
        ( A ) NAME/KEY: CDS
        ( B ) LOCATION: complement (18..33)

( x i ) SEQUENCE DESCRIPTION: SEQ ID NO:3:

ACGCGTGGTA CCTCGAGTCA CGCGACACAA GCT      33

(2) INFORMATION FOR SEQ ID NO:4:

(i) SEQUENCE CHARACTERISTICS:
        (A) LENGTH: 37 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Toxoplasma gondii
        (C) INDIVIDUAL ISOLATE: P30 antigen gene (vii) IMMEDIATE SOURCE:
        (B) CLONE: Primer #3

(ix) FEATURE:
        (A) NAME/KEY: 5'UTR
        (B) LOCATION: 1..20

(ix) FEATURE:
        (A) NAME/KEY: CDS
        (B) LOCATION: 21..37

(xi) SEQUENCE DESCRIPTION: SEQ ID NO:4:

GTCGACCCCG GGTCTAGACC ATGGCATCGG ATCCCCC      37

(2) INFORMATION FOR SEQ ID NO:5:

(i) SEQUENCE CHARACTERISTICS:
        (A) LENGTH: 41 base pairs
        (B) TYPE: nucleic acid
        (C) STRANDEDNESS: single
        (D) TOPOLOGY: linear (ii) MOLECULE TYPE: cDNA (iii) HYPOTHETICAL: YES (iv) ANTI-SENSE: NO (vi) ORIGINAL SOURCE:
        (A) ORGANISM: Toxoplasma gondii
        (C) INDIVIDUAL ISOLATE: P30 antigen gene (vii) IMMEDIATE SOURCE:
        (B) CLONE: Primer #4

(ix) FEATURE:
        (A) NAME/KEY: 3'UTR
        (B) LOCATION: complement (1..17)

(ix) FEATURE:
        (A) NAME/KEY: CDS
        (B) LOCATION: complement (18..41)

(xi) SEQUENCE DESCRIPTION: SEQ ID NO:5:

ACGCGTGGTA CCTCGAGTTA TGCTGACCCT GCAGCCCGG C      41

(2) INFORMATION FOR SEQ ID NO:6:

(i) SEQUENCE CHARACTERISTICS:
        (A) LENGTH: 35 base pairs
        (B) TYPE: nucleic acid
        (C) STRANDEDNESS: single
        (D) TOPOLOGY: linear (ii) MOLECULE TYPE: cDNA ( i i i ) HYPOTHETICAL: YES ( i v ) ANTI-SENSE: NO ( v i ) ORIGINAL SOURCE:
    ( A ) ORGANISM: Toxoplasma gondii
    ( C ) INDIVIDUAL ISOLATE: P30 antigen gene ( v i i ) IMMEDIATE SOURCE:
    ( B ) CLONE: Primer #5

( i x ) FEATURE:
    ( A ) NAME/KEY: 5'UTR
    ( B ) LOCATION: 1..18

( i x ) FEATURE:
    ( A ) NAME/KEY: CDS
    ( B ) LOCATION: 19..35

( x i ) SEQUENCE DESCRIPTION: SEQ ID NO:6:

GTCGACTCTA GACCCGGGAT GGCATCGGAT CCCCC      35

( 2 ) INFORMATION FOR SEQ ID NO:7:

( i ) SEQUENCE CHARACTERISTICS:
    ( A ) LENGTH: 34 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
    ( A ) ORGANISM: Toxoplasma gondii
    ( C ) INDIVIDUAL ISOLATE: P30 antigen gene ( v i i ) IMMEDIATE SOURCE:
    ( B ) CLONE: Primer #6

( i x ) FEATURE:
    ( A ) NAME/KEY: 3'UTR
    ( B ) LOCATION: complement (1..18)

( i x ) FEATURE:
    ( A ) NAME/KEY: CDS
    ( B ) LOCATION: complement (19..34)

( x i ) SEQUENCE DESCRIPTION: SEQ ID NO:7:

ACGCGTGGTA CCGAATTCTC ACGCGACACA AGCT      34

( 2 ) INFORMATION FOR SEQ ID NO:8:

( i ) SEQUENCE CHARACTERISTICS:
    ( A ) LENGTH: 110 base pairs
    ( B ) TYPE: nucleic acid
    ( C ) STRANDEDNESS: single
    ( D ) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
    ( A ) ORGANISM: Toxoplasma gondii
    ( C ) INDIVIDUAL ISOLATE: tissue plasminogen activator signal
        seq./P30 antigen gene ( v i i ) IMMEDIATE SOURCE:
    ( B ) CLONE: Primer #7

( i x ) FEATURE:
 (A) NAME/KEY: 5'UTR
 (B) LOCATION: 1..20

( i x ) FEATURE:
 (A) NAME/KEY: CDS
 (B) LOCATION: 21..89

( i x ) FEATURE:
 (A) NAME/KEY: CDS
 (B) LOCATION: 90..110

( x i ) SEQUENCE DESCRIPTION: SEQ ID NO:8:

GTCGACCCCG GGTCTAGACC ATGGATGCAA TGAAGAGAGG GCTCTGCTGT GTGCTGCTAC 60

TGTGTGGAGC AGTCTTCGTT TCGCCCAGCT CGGATCCCCC TCTTGTTGCC 110

( 2 ) INFORMATION FOR SEQ ID NO:9:

( i ) SEQUENCE CHARACTERISTICS:
 (A) LENGTH: 37 base pairs
 (B) TYPE: nucleic acid
 (C) STRANDEDNESS: single
 (D) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
 (A) ORGANISM: plasmid
 (C) INDIVIDUAL ISOLATE: pGEX:nP30.771

( v i i ) IMMEDIATE SOURCE:
 (B) CLONE: Primer #8

( i x ) FEATURE:
 (A) NAME/KEY: 5'UTR
 (B) LOCATION: 1..20

( i x ) FEATURE:
 (A) NAME/KEY: CDS
 (B) LOCATION: 21..37

( x i ) SEQUENCE DESCRIPTION: SEQ ID NO:9:

GTCGACCCCG GGTCTAGACC ATGTCCCTA TACTAGG 37

( 2 ) INFORMATION FOR SEQ ID NO:10:

( i ) SEQUENCE CHARACTERISTICS:
 (A) LENGTH: 33 base pairs
 (B) TYPE: nucleic acid
 (C) STRANDEDNESS: single
 (D) TOPOLOGY: linear ( i i ) MOLECULE TYPE: cDNA ( i i i ) HYPOTHETICAL: YES ( i v ) ANTI-SENSE: NO ( v i ) ORIGINAL SOURCE:
 (A) ORGANISM: plasmid
 (C) INDIVIDUAL ISOLATE: pGEX:nP30.771

( v i i ) IMMEDIATE SOURCE:
 (B) CLONE: Primer #9

( i x ) FEATURE:
 (A) NAME/KEY: 3'UTR
 (B) LOCATION: complement (1..17)

( i x ) FEATURE:

( A ) NAME/KEY: CDS
( B ) LOCATION: complement (18..33)

( x i ) SEQUENCE DESCRIPTION: SEQ ID NO:10:

ACGCGTGGTA CCTCGAGTCA GTCAGTCACG ATG    3 3

1

RECOMBINANT PACKAGING DEFECTIVE SINDBIS VIRUS VACCINES

This is a continuation of copending application Ser. No. 08/015,414, filed on Feb. 8, 1993.

This invention was made at least in part with government support under SBIR Grant No. 5R44-AI-30834-03, awarded by the National Institutes of Health to Dr. Cheng Xiong. The government has certain rights to this invention.

FIELD OF THE INVENTION

The present invention relates to novel recombinant live alphavirus vaccines and their use to protect animals from, for example, infectious or metabolic diseases.

BACKGROUND

Live vaccines, and particularly viral vaccines, have been associated with longer-lasting immunity than inactivated vaccines. However, one disadvantage of live vaccines has been their ability to revert to virulence. In an attempt to overcome this problem, several viral and bacterial systems, such as poxviruses, herpesviruses, adenoviruses, Salmonella, and BCG (Bacillus Calmette-Guerin), have been genetically manipulated to generate vectors containing heterologous antigen genes in order to immunize a host with a vaccine in which the antigens are presented in a "live" configuration (i.e., in which the antigens are exposed on the outside of a cell membrane or viral coat). See, for example, the following two review articles: Esposito et al., pp. 195–247, 1989, Advances in Veterinary Science and Comparative Medicine, Vol. 33; Dougan et al., pp. 271–300, 1989, Advances in Veterinary Science and Comparative Medicine, Vol. 33. However, none of these systems has yet been commercialized.

Alphaviruses, which are members of the togavirus family, are attractive vaccine carriers because they have a wide host range. However, a number of alphaviruses, including Semliki Forest virus, are pathogenic. In contrast, the alphavirus Sindbis virus, has not been associated with natural disease in humans or animals. The genomes of several alphaviruses, including Sindbis virus, Semliki Forest virus, and Ross River virus, have been cloned and their nucleotide sequences determined; see Strauss et al., pp. 91–110, 1984, Virology, Vol. 133; Liljestrom et al., pp. 4107–4113, 1991, J. Virology, Vol. 65; Faragher et al., pp. 509–526, Virology, Vol. 163.

Alphaviruses are RNA viruses with a positive polarity RNA genome of about 12,000 nucleotides in length which sediments at about 49S. Sindbis virus 49S RNA is capped at the 5' end and polyadenylated at the 3' end. The 5' two-thirds of the 49S RNA encodes alphavirus nonstructural polypeptides (e.g., nsP1, nsP2, nsP3, and nsP4) required for replication and transcription. Replication of the 49S RNA results in a full-length negative polarity copy which serves both as a template for new 49S genomic RNA and as a template for transcription of a 26S subgenomic RNA molecule which corresponds to the 3' third of the genome and contains the genes for the alphavirus structural polypeptides (e.g., capsid polypeptide C, envelope glycopolypeptides E1 and E2, E3 and 6K). Expression of the 26S subgenomic RNA is under the control of a subgenomic promoter, which is located on the genome as shown in FIG. 1.

Both Sindbis and Semliki Forest viral expression vectors have been used to produce heterologous proteins in cell culture. For example, Sindbis virus vectors have been used to produce chloramphenicol acetyltransferase and tissue plasminogen activator (Xiong et al., pp. 1188–1191, 1989, Science, Vol. 243; Huang et al., pp. 85–91, 1989, Virus Genes, Vol. 3), and Semliki Forest virus vectors have been used to produce the human transferrin receptor, mouse dihydrofolate reductase, chick lysozyme, and beta-galactosidase (Liljestrom et al., pp. 1356–1361, 1991, Bio/Technology, Vol. 9). However, the inventors are unaware of the use of a live alphavirus-based recombinant vaccine to protect an animal from infectious or metabolic diseases.

There are a number of diseases from which an animal may be protected if the animal is given a vaccine containing a protein that blocks the disease-causing agent from replicating and spreading infection. In some cases, effective antigens have been identified that can be used to immunize an animal, but effective systems to deliver such vaccines have yet to be developed. One disease in which the latter is the case is toxoplasmosis.

Toxoplasmosis is caused by the obligate intracellular protozoan parasite Toxoplasma gondii. Most warm-blood animals are susceptible to infection by the parasite, and cats are an obligate host of the parasite. Humans and animals can acquire toxoplasmosis from ingestion of infectious oocysts shed by cats, ingestion of undercooked meat containing Toxoplasma gondii tissue cysts, and congenital transmission. Toxoplasmosis is generally asymptomatic in healthy human adults, but can cause severe disease and death in immuno-compromised individuals, such as those with AIDS (acquired immunodeficiency syndrome). In humans, an active infection in a pregnant woman can cause severe fetal abnormalities resulting in impaired vision and mental retardation. Toxoplasmosis also causes disease and abortions in sheep and pigs.

A number of Toxoplasma gondii antigens have been characterized which are present at different stages of the parasite's life cycle. The P30 antigen (P30), one of the major surface antigens of the tachyzoite stage of Toxoplasma gondii, is conserved in most strains of the parasite. P30 is highly antigenic, eliciting high antibody titers in infected individuals (e.g., Partanen et al., p. 133, 1984, J. Clin. Microbiol., Vol. 20; Potusman et al., p. 650, 1986, J. Infect. Dis., Vol. 154; Sharma et al., p. 977, 1983, J. Immunol., Vol. 131). Native P30 has been used to immunize mice and protect them against a lethal challenge with virulent Toxoplasma gondii (Khan et al., pp. 3501–3506, 1991, J. Immunol., Vol. 147; Bulow et al., pp. 3496–3500, 1991, J. Immunol., Vol. 147). The supply of native P30, however, has to date been too limited to make the isolation and use of such a native protein as a vaccine feasible.

The gene encoding P30 has been isolated and sequenced by Burg et al., pp. 3584–3591, 1988, J. Immunol., Vol. 141. Other cloned Toxoplasma gondii genes include those that encode tachyzoite antigens P22 (Prince et al., pp. 97–106, 1990, Molecular and Biochemical Parasitology, Vol. 43) and P23 (Cesbron-Delauw et al., pp. 7537–7541, 1989, Proc. Natl. Acad. Sci. USA, Vol. 86) as well as antigens of a variety of molecular weights (e.g., Capron et al., PCT International Publication WO 89/12683, 1989; Johnson et al., pp. 127–132, 1991, Gene, Vol. 99; Knapp et al., European Patent Application Publication No. 431,541, 1991; Matsuura et al., European Patent Application Publication No. 391,319, 1990; Prince et al., pp. 3–14, 1989, Molecular and Biochemical Parasitology, Vol. 34; Saavebra et al., pp. 1975–1982, 1991, J. Immunol., Vol. 147). Several of these genes have been expressed in E. coli, but the present investigators are unaware of any investigations concerning whether or not such recombinant proteins can be used to protect animals from Toxoplasma gondii infection.

Thus, there is a need for new and improved methods to vaccinate animals, particularly to protect animals from toxoplasmosis caused by *Toxoplasma gondii* infection. In addition, there is a need to develop an improved vaccine delivery system to protect animals from other diseases, such as those caused by metabolic disorders or infectious agents such as protozoan parasites, helminth parasites, ectoparasites, fungi, bacteria, and viruses.

SUMMARY OF THE INVENTION

The present invention relates to a new method to protect animals from disease using a recombinant virus particle vaccine comprising a recombinant molecule packaged in an alphavirus coat. When the recombinant virus particle vaccine of the present invention is administered to an animal, the virus particle is able to infect cells within the animal. Infected cells are able to express nucleic acid sequences present on the recombinant molecule to produce compounds, such as proteins and RNAs, capable of protecting the animal from a variety of diseases. Using methods taught in the present invention, vaccines can be generated that are capable of protecting an animal from any disease for which a protective protein or protective RNA can be produced. As such, the present invention is of extremely broad scope and includes a wide variety of vaccines that have a variety of applications.

One embodiment of the present invention is a recombinant virus particle vaccine that includes a recombinant molecule packaged in an alphavirus coat, the vaccine being capable of protecting an animal from disease when administered to the animal in an effective amount. The recombinant molecule includes a nucleic acid sequence that encodes a protective compound, such as a protective protein or protective RNA, operatively linked to a packaging-defective alphavirus expression vector that is capable of directing transcription (and preferably also replication) of the recombinant molecule. Animals administered the vaccine are able to produce the protective compound encoded by the nucleic acid sequence contained in the recombinant molecule of the vaccine and thereby are protected from any disease that the protective compound can effectively neutralize or otherwise counteract.

Nucleic acid sequences of the present invention can be engineered to permit protective compounds produced by infected cells to remain inside the cell, to be secreted from the cell, or to be attached to the outer cell membrane. Protective compounds can, for example, include protective fusion proteins which consist of more than one protective protein. One embodiment is a vaccine that includes a recombinant virus particle vaccine in combination with a protective protein that has essentially the same or similar function to the protective protein encoded by the nucleic acid sequence contained within the virus particle. Furthermore, vaccines of the present invention can, but need not, include immunopotentiators.

Preferred vaccines are those that protect animals from diseases caused by protozoan parasites, helminth parasites, ectoparasites, fungi, bacteria, and viruses; particularly those vaccines that protect animals from diseases caused by infectious agents of the genera Toxoplasma, Dirofilaria, Cryptosporidium, Eimeria, Neospora, Isospora, Plasmodium, Babesia, Theileria, Hepatozoon, Encephalitozoon, Nosema, Pneumocystis, Cryptococcus, Candida, and Histoplasma; and even more particularly vaccines that protect animals against infection by *Toxoplasma gondii, Dirofilaria immitis,* or Cryptosporidium.

Upon administration to an animal, preferred vaccines of the present invention are capable of effecting production of a protective protein that can elicit an immune response to protect the animal from, for example, an infectious agent. Other preferred vaccines are capable of eliciting production of antisense RNA molecules to protect an animal from disease. Particularly preferred vaccines contain nucleic acid sequences that encode at least one antigen, preferably *Toxoplasma gondii* P30 or a functional equivalent thereof, capable of eliciting an immune response to protect an animal from toxoplasmosis.

One embodiment of the present invention are nucleic acid sequences that each encodes one of the following modified *Toxoplasma gondii* P30 antigens (a) a P30 antigen lacking amino terminal hydrophobic residues, (b) a P30 antigen lacking carboxyl terminal hydrophobic residues, or (c) a P30 antigen lacking both amino terminal and carboxyl terminal hydrophobic residues.

Expression of nucleic acid sequences of the present invention is effected by alphavirus expression vectors to which the nucleic acid sequences are operatively linked. Preferred alphavirus expression vectors include Sindbis virus expression vectors, Semliki Forest virus expression vectors, Ross River virus expression vectors, and hybrids thereof, with Sindbis virus expression vectors being more preferred. According to one embodiment, a nucleic acid sequence of the present invention is operatively linked to an alphavirus subgenomic promoter, which preferably is a Sindbis virus subgenomic promoter, a Semliki Forest virus subgenomic promoter, a Ross River virus subgenomic promoter, or a hybrid thereof, with Sindbis virus subgenomic promoters being more preferred.

The present invention also relates to a method for protecting an animal from disease by administering to such an animal an effective amount of a recombinant virus particle vaccine of the present invention. Preferred animals to vaccinate include mammals, insects, and birds, with humans, pigs, sheep, dogs, cats, cattle, horses, and poultry being more preferred. Vaccines can be administered in a variety of ways including by injection, by oral application, by nasal application, or by topical application. According to one embodiment, a protective protein containing amino acids encoded by the nucleic acid sequence contained in the virus particle is also administered to the animal either prior to, following, or both prior to and following administration of the recombinant virus particle vaccine in order to enhance the immunogenic response.

Another aspect of the present invention involves recombinant molecules and the production thereof. Recombinant molecules of the present invention can be generated by: (a) producing a nucleic acid sequence encoding a protective compound; (b) producing a packaging-defective alphavirus expression vector capable of directing transcription (and preferably also replication) of the recombinant molecule; and (c) operatively linking the nucleic acid sequence of (a) to the expression vector of (b) to obtain a recombinant molecule in which expression of the nucleic acid sequence is controlled by the expression vector.

The present invention also relates to a method to produce recombinant virus particle vaccines, which includes transfecting a recombinant molecule of the present invention into a host cell, preferably a mammalian, insect, or avian cell, in such a manner that culturing of the transfected cell yields recombinant virus particles. For example, a recombinant molecule can be co-transfected into a host cell with an alphavirus packaging vector that is capable of effecting packaging of the recombinant molecule into a virus particle, but is essentially incapable of self-packaging. Preferred packaging vectors include Sindbis virus packaging vectors, Semliki Forest virus packaging vectors, Ross River virus packaging vectors, and hybrids thereof, with Sindbis virus packaging vectors being more preferred. Alternatively, the host cell to be transfected by the recombinant molecule can already contain the genetic information required to effect packaging of the recombinant molecule into a virus particle. Transfected cells are subsequently cultured to produce virus particles, which are then recovered and formulated into a vaccine.

A preferred embodiment of the present invention is a method to protect an animal from toxoplasmosis by administering to the animal an effective amount of a recombinant virus particle vaccine. The recombinant virus particle vaccine includes a recombinant molecule containing a nucleic acid sequence encoding a *Toxoplasma gondii* P30 antigen or functional equivalent of the antigen, the nucleic acid sequence being operatively linked to a packaging-defective Sindbis virus expression vector capable of directing replication and transcription of the recombinant molecule. The vaccine of the present invention when administered to an animal is preferably capable of infecting the animal so as to cause the production of P30 antigen which subsequently acts to elicit an immune response capable of protecting the vaccinated animal from toxoplasmosis.

BRIEF DESCRIPTION OF THE FIGURES

FIG. 1 is a schematic drawing depicting an alphavirus RNA genome and subgenomic RNA.

FIG. 3 depicts a hydrophilicity plot of *Toxoplasma gondii* P30 antigen.

FIG. 5 compares schematic drawings of Sindbis virus expression vectors SV1 and SV2 with a schematic drawing of a full-length Sindbis virus vector.

FIG. 6 schematically depicts the derivation of Sindbis virus packaging vector PV1.

DETAILED DESCRIPTION OF THE INVENTION

The present invention includes a recombinant virus particle vaccine, methods to produce the vaccine, and methods to use the vaccine, preferably to immunize animals against infectious or metabolic diseases.

A recombinant virus particle vaccine of the present invention includes recombinant genetic information packaged in a viral coat. As such, a vaccine of the present invention is essentially a live vaccine and is advantageous because live vaccines are believed to confer more vigorous and longer-lasting immunity. While not being bound by theory, it is believed that such advantages are due to the ability of the genetic information carried by the virus particle vaccine to enter the cells of the vaccinated animal, replicate itself, and direct the expression of a protective compound, such as a protective protein (e.g., an immunogenic protein) or a protective RNA (e.g., an antisense RNA) for extended periods of time. Thus, the vaccine need not be administered frequently and, in fact, the virus particle vaccine essentially can function as a self-booster.

In addition, since the genetic information is packaged in a viral coat, the genetic information is protected from degradation and is injected into host cells by the normal route of infectivity, that is through normal cellular receptors that recognize and take up viruses. Recombinant virus particle vaccines of the present invention have a wide host range by virtue of their being able to infect multiple species and cell types. Moreover, since the genetic information present in the vaccine of the present invention is packaging-defective (i.e., unable to effect packaging of the genetic information into a viral coat), essentially no infectious virus is produced by the infected cells.

A recombinant virus particle vaccine of the present invention includes a recombinant molecule packaged in an alphavirus coat. As used herein, an "alphavirus coat" is a viral coat containing at least one alphavirus structural polypeptide. As used herein, "a recombinant molecule" includes (a) a nucleic acid sequence encoding a protective compound, such as a protective protein or protective RNA; and (b) an alphavirus expression vector which is operatively linked to the nucleic acid sequence and which is packaging-defective (i.e., not capable of effecting packaging of the recombinant molecule into a virus). The present invention includes RNA recombinant molecules as well as DNA recombinant molecules from which the RNA recombinant molecules can be transcribed. As used herein, a "protective protein" is a protein that, when produced by an animal administered the vaccine, is able to treat, ameliorate, or prevent an infectious or metabolic disease in that animal. Similarly, a "protective RNA" is an RNA molecule that, when produced by an animal administered the vaccine, is able to treat, ameliorate, or prevent an infectious or metabolic disease in that animal. As used herein, "operatively linked" means that the nucleic acid sequence is joined (i.e., ligated) to the alphavirus expression vector in such a manner that regulatory signals present on the vector (e.g., promoters) lead to the expression of the nucleic acid sequence, ultimately leading to the production of the corresponding protective protein (i.e., the protein encoded by the nucleic acid sequence) or RNA (e.g., an antisense RNA or an RNA-based drug) that blocks disease.

A vaccine of the present invention delivers to a vaccinated animal a nucleic acid sequence of the present invention (i.e., an RNA or DNA sequence that encodes a protective protein or RNA) plus the proper alphavirus regulatory sequences so that the vaccinated animal can produce a protective protein or RNA corresponding to that nucleic acid sequence. Essentially any nucleic acid sequence that encodes a protective protein or RNA can be used in the present invention. A protective protein of the present invention can be, for example, an immunogen that elicits an immune response which will protect an animal from the corresponding infectious disease or some other compound (e.g., toxins, enzymes, antibodies, or other binding proteins) that neutralizes the infectious agent which causes the disease. A protective RNA of the present invention can be, for example, an RNA-based drug or an antisense RNA that effectively prevents the expression of a detrimental protein, thereby protecting an animal from disease. As such, it is within the scope of the present invention to develop vaccines against a variety of infectious diseases such as those caused by protozoan parasite, helminth parasite, ectoparasite, fungal, bacterial, or viral infectious agents. It is also within the scope of the present invention to develop vaccines against a variety of metabolic diseases, such as Cushing's disease or cancer preferably using a vaccine encoding an antisense RNA.

Figure 2:
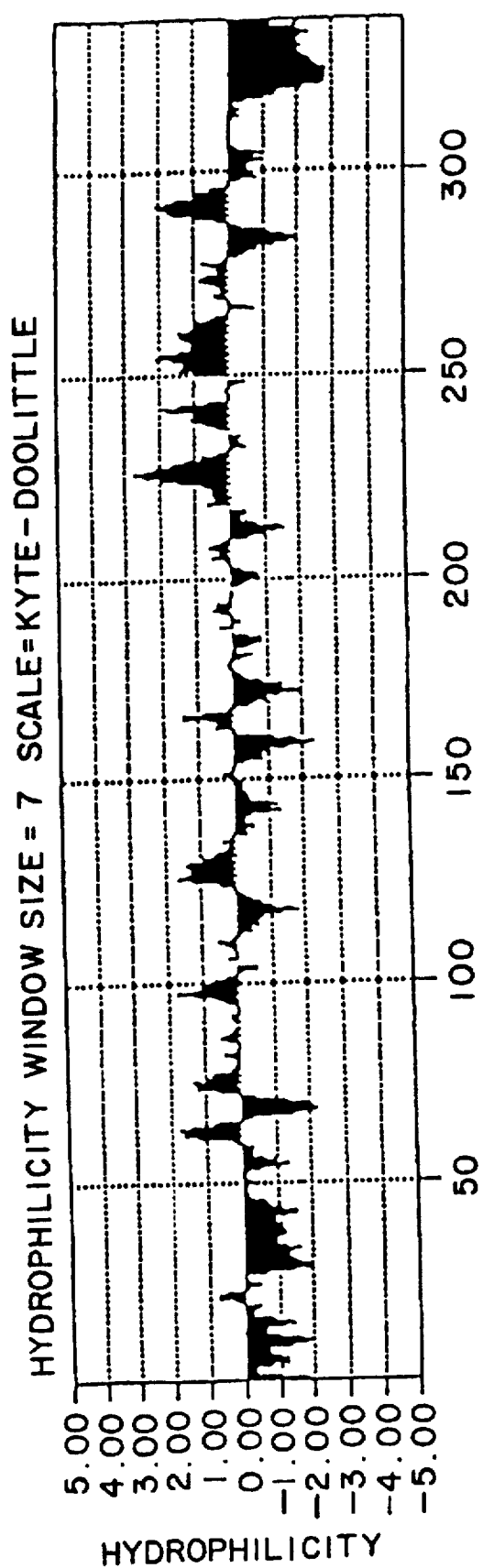
FIG. 2 depicts the DNA (SEQ ID NO:1) and deduced amino acid sequence of *Toxoplasma gondii* P30 antigen (from Burg et al., ibid.).

A preferred nucleic acid sequence of the present invention encodes a protective protein capable of eliciting an immune response, including both humoral and cell-mediated immunity, to protect the animal from the disease. As used herein, the phrases "to protect an animal from infection" and "to protect an animal from infectious disease" refer to the ability of the protective protein or RNA (and, hence, the vaccine) to treat, ameliorate, or prevent an infectious disease in the vaccinated animal, particularly by interfering with the infectious agent that causes the disease. Similarly, the phrase "to protect an animal from metabolic disease" refers to the ability of the protective protein or RNA to treat, ameliorate, or prevent a metabolic disease in the vaccinated animal.

Nucleic acid sequences of the present invention can be isolated from natural sources, can be obtained by mutating natural isolates using classic or recombinant DNA techniques, or can be synthesized chemically. As used herein, an isolated nucleic acid sequence refers to a nucleic acid sequence that encodes a protective protein or RNA and that has been separated from its natural milieu either by removing the sequence from its natural location using, for example, recombinant DNA technology or by producing the sequence synthetically. Nucleic acid sequences of the present invention include those that encode naturally-occurring (i.e., native) protective proteins as well as those that encode functional equivalents thereof (i.e., functionally equivalent protective proteins). As used herein, a "functionally equivalent" protective protein is a protein that has substantially the same biological activity as the naturally-occurring protective protein; that is, the functionally equivalent protective protein is capable of protecting an animal from infectious disease. Nucleic acid sequences that encode functionally equivalent protective proteins are herein referred to as functionally equivalent nucleic acid sequences and include nucleic acid sequences having deletions, additions, inversions, and/or substitutions which, in spite of the modifications, encode protective proteins. The minimal size of a functionally equivalent protective protein is the shortest length of amino acids required to protect an animal from an infectious disease. It is believed that the minimal size of a protective protein required to elicit an immune response is at least about seven amino acids, since the protective protein must be of sufficient size to elicit an immune response effective against, for example, an infectious agent. Protective proteins encoded by the nucleic acid sequences of the present invention can be unmodified or can be modified by post-translation mechanisms, including glycosylation, acetylation, phosphorylation, and carboxyl-terminal amidation.

Additional nucleic acid sequences of the present invention include nucleic acid sequences that encode RNA-based drugs or antisense RNAs. As used herein, an "RNA-based drug" is any RNA molecule that is of sufficient size and/or structure to be able to interact with an intra- or extra-cellular component in order to prevent, treat, or ameliorate a disease otherwise caused by that component. As used herein an "antisense RNA" is any RNA that is capable of substantially preventing expression of a detrimental protein. As such, a nucleic acid sequence encoding such an RNA can be of any size and structure that, when expressed, will yield an antisense RNA having the defined function.

A functionally equivalent nucleic acid sequence can be obtained using methods known to those skilled in the art. See, for example, Sambrook et al., *Molecular Cloning: A Laboratory Manual*, Cold Spring Harbor Labs Press, 1989, which is incorporated herein by reference in its entirety. For example, nucleic acid sequences can be modified using a variety of techniques including, but not limited to, classic mutagenesis techniques and recombinant DNA techniques, such as site-directed mutagenesis, chemical treatment of a nucleic acid to induce mutations, restriction enzyme cleavage of a nucleic acid fragment, ligation of nucleic acid fragments, polymerase chain reaction (PCR) amplification and/or mutagenesis of selected regions of a nucleic acid sequence, synthesis of oligonucleotide mixtures and ligation of mixture groups to "build" a mixture of nucleic acid sequences, and combinations thereof. Functionally equivalent nucleic acids can be selected from a mixture of modified nucleic acid sequences by screening for the function of the protein or antisense RNA encoded by the nucleic acid sequence. A number of screening techniques are known to those skilled in the art including, but not limited to, functional assays and binding assays. In one embodiment, a nucleic acid sequence that encodes a functionally equivalent *Toxoplasma gondii* antigen can be selected by its ability to elicit an immune response capable of protecting an animal from toxoplasmosis.

The present invention particularly involves recombinant virus particle vaccines that protect animals from infectious agents such as protozoan parasites, helminth parasites, ectoparasites, fungi, bacteria and viruses. As used herein, Microsporidia organisms are classified as protozoan parasites. As used herein, Pneumocystis organisms are classified as fungi, although there is still controversy as to whether or not they should be classified as protozoa or fungi. Preferably, vaccines of the present invention protect animals from protozoan parasites, helminth parasites, ectoparasites, and/or fungi such as those that cause heartworm, malaria, coccidiosis, toxoplasmosis, or other AIDS-related opportunistic infections. More preferably, the vaccine is effective against parasites of the genera Toxoplasma, Dirofilaria, Cryptosporidium, Eimeria, Neospora, Isospora, Plasmodium, Babesia, Theileria, Hepatozoon, Encephalitozoon (e.g., *Encephalitozoon cuniculi* or *Encephalitozoon hellem*), Nosema (e.g., *Nosema corneum*), Pneumocystis (e.g., *Pneumocystis carinii*), Cryptococcus, Candida, and Histoplasma. The vaccine is even more preferably effective against *Toxoplasma gondii*, *Dirofilaria immitis*, or Cryptosporidium parasites. Therefore, preferred nucleic acid sequences of the present invention are those that encode protective proteins that protect animals from infectious diseases caused by protozoan parasites, helminth parasites, ectoparasites, fungi, bacteria or viruses. More preferred nucleic acid sequences are those that encode protective proteins that protect animals from protozoan parasites, helminth parasites, ectoparasites, and/or fungi such as those that cause heartworm, malaria, coccidiosis, toxoplasmosis, or other AIDS-related opportunistic infections.

A particularly preferred nucleic acid sequence of the present invention encodes a *Toxoplasma gondii* antigen that is capable of eliciting an immune response to protect an animal from infection by *Toxoplasma gondii*, which is a parasite that causes toxoplasmosis. *Toxoplasma gondii* antigens useful in the present invention include, but are not limited to, tachyzoite antigens P30, P23, and P22, and other *Toxoplasma gondii* antigens with molecular weights of about 25, about 28, about 30, about 35, about 41, about 54, about 66, and about 68 kilodaltons.

A more preferred nucleic acid sequence for use in the present invention is one encoding a protective protein corresponding to the *Toxoplasma gondii* P30 antigen, the major surface antigen of the tachyzoite stage of *Toxoplasma gondii* infection. P30 is advantageous because it has been shown to protect mice from virulent *Toxoplasma gondii* challenge (Khan et al., ibid.; Bulow et al., ibid.). As such, the gene encoding the P30 antigen, which has been isolated and sequenced by Burg et al., ibid., is particularly useful in the present invention. The nucleic acid sequence of the *Toxoplasma gondii* P30 gene isolated and sequenced by Burg et al. (SEQ ID NO:1), and the amino acid sequence deduced from the gene, are shown in FIG. 2.

Another aspect of the present invention includes novel nucleic acid sequences that encode modified P30 antigens that are functionally equivalent to the natural P30 protein; that is, the modified antigens are capable of eliciting an immune response against *Toxoplasma gondii* that protects the animal from toxoplasmosis. These nucleic acid sequences include, but are not limited to, modified nucleic acid sequences that encode P30 antigens from which amino acids possessing potentially troublesome hydrophobic groups (e.g., at the amino and/or carboxyl termini, as necessary) have been removed, P30 antigens which can be secreted from the cells that produce them, and P30 antigens that are able to attach to the outer membranes of the cells that produce them.

When an alphavirus infects a cell, the virus takes over the host transcription and translation machinery but does not usually kill the cell. Thus, for protective proteins that are often protective only when outside the host cell (e.g., immunogens), it is preferred for such protective proteins to be secreted from the infected cell into a bodily fluid such as the bloodstream, to become attached to the outer membrane of the infected cell, or to be released from infected cells upon cell death.

In addition, the amino and carboxyl termini of natural *Toxoplasma gondii* P30 antigens are hydrophobic, particularly in the regions spanning amino acid residues from about 1 through about 45 at the amino terminus and spanning amino acid residues from about 309 through about 336 at the carboxyl terminus (assuming that the methionine at position 1 corresponds to the first amino acid of the primary translation product, as shown in FIG. 2 and in the hydrophilicity plot in FIG. 3). While not being bound by theory, it is believed that these hydrophobic terminal residues of P30 antigen can lead to protein insolubility problems as well as to an inability to efficiently secrete P30 antigen from the cell in which it is produced. As such, a particularly preferred nucleic acid sequence of the present invention is one in which a nucleic acid signal segment is joined to a nucleic acid sequence encoding a modified *Toxoplasma gondii* P30 antigen from which hydrophobic amino and carboxyl terminal residues have been removed in such a manner as to effectively direct secretion of the encoded protective protein from the cell infected by the recombinant virus particle vaccine.

As used herein, a "nucleic acid signal segment" is a stretch of nucleotides that encodes a signal sequence peptide. Signal sequence peptides, which usually range in size from about 15 to about 30 amino acids, are thought to initiate the transport of a protein across the membrane as an early step in the secretion process. In order to direct secretion of a protective protein of the present invention, the signal sequence peptide is joined to the amino terminus of the protective protein to be secreted. Such a protein is encoded by a nucleic acid signal segment operatively joined to the nucleic acid sequence encoding the protective protein.

Another preferred nucleic acid sequence of the present invention is one in which a nucleic acid signal segment is substituted for the nucleic acid segment encoding the amino terminal hydrophobic residues of P30 and in which a nucleic acid segment encoding a "hook" or "anchor" is substituted for the nucleic acid segment encoding the carboxyl terminal hydrophobic residues of P30 in order to cause the functionally equivalent protective protein to be attached to the outer membrane of the cell that produces it. Suitable "hooks" include the "hook" carboxyl termini of Class II proteins, such as immunoglobulins.

Suitable nucleic acid signal segments for use in the present invention include, but are not limited to, nucleic acid signal segments of tissue plasminogen activator (t-PA), interferon alpha, and interleukin-3. A preferred nucleic acid signal segment is a t-PA nucleic acid signal segment, preferably encoding the initial about 23 amino acids of the t-PA primary translation product.

Figure 4:
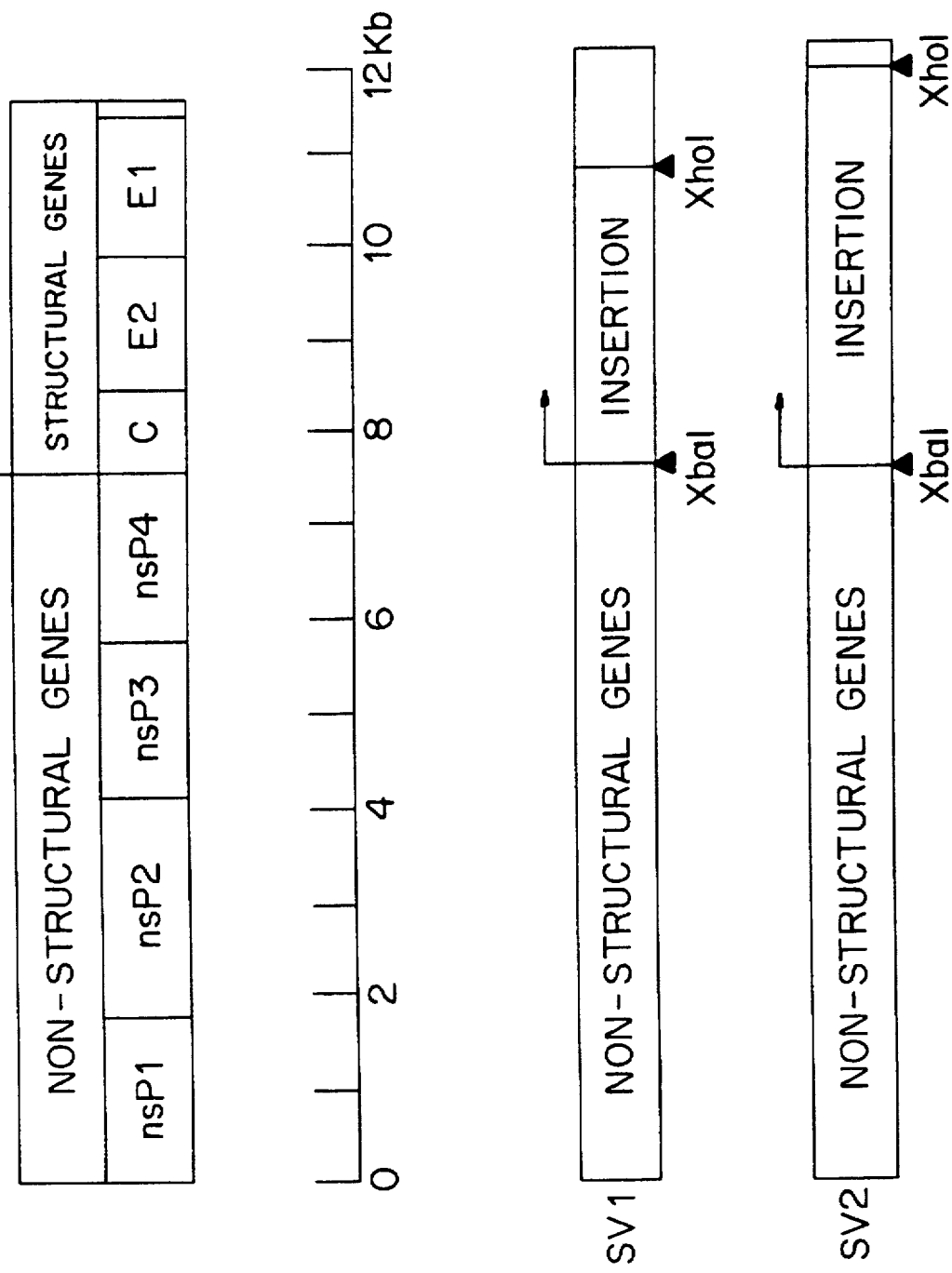
FIG. 4 includes schematic drawings of several nucleic acid sequences that encode functionally equivalent P30 antigens.

Referring to FIG. 4, particularly preferred nucleic acid sequences of the present invention are nP30.1008 which encodes P30 antigen P30.336, corresponding to the protein sequence shown in FIG. 2; nP30.873 which encodes P30.291; nP30.924 which encodes P30.308; nP30.789 which encodes P30.263; nP30.867SS which encodes P30.289SS, nP30.924SS which encodes P30.308SS, and nP30.783SS which encodes P30.261SS. Note that although the nucleic acid sequences diagrammed in FIG. 4 are flanked by XbaI and XhoI restriction endonuclease sites, such nucleic acid sequences can be flanked by a variety of restriction enzyme sites to allow easy insertion of the sequences into a variety of expression and cloning vectors. P30.291 spans amino acids from about 46 through about 336 of P30, as numbered in FIG. 2, and as such, lacks amino terminal hydrophobic residues. P30.308 spans amino acids from about 1 through about 308, as numbered in FIG. 2, and as such, lacks carboxyl terminal hydrophobic residues. P30.263 spans amino acids from about 46 through about 308, as numbered in FIG. 2, and as such, lacks both amino and carboxyl terminal hydrophobic residues. Prior to secretion, P30.289SS contains a t-PA signal sequence of about 23 amino acids joined to the amino terminus of a modified P30 protein that spans amino acids from about 48 through about 336 of P30, as numbered in FIG. 2, and as such, lacks P30 amino terminal hydrophobic residues. (Note that Burg et al., ibid., have predicted that *Toxoplasma gondii* P30 is cleaved between amino acids 47 and 48 during maturation.) Prior to secretion, P30.308SS contains a t-PA signal sequence of about 23 amino acids joined to the amino terminus of a modified P30 protein that spans amino acids from about 1 through about 308 of P30, as numbered in FIG. 2, and as such, lacks P30 carboxyl terminal hydrophobic residues. Prior to secretion, P30.261SS contains a t-PA signal sequence of about 23 amino acids joined to the amino terminus of a modified P30 protein that spans amino acids from about 48 through about 308 of P30, as numbered in FIG. 2, and as such, lacks P30 amino and carboxyl terminal hydrophobic residues. Additional preferred nucleic acid sequences of the present invention include (a) nP30.771, described in Example 1G, which encodes P30.257, a modified P30 protein spanning amino acids from about 49 through about 305, as numbered in FIG. 2, and as such, lacks P30 amino and carboxyl terminal residues; and (b) nP30.771SS which encodes P30.257SS.

Additional nucleic acid sequences of the present invention include nucleic acid fusion fragments which encode multivalent protective fusion proteins. A nucleic acid fusion fragment is produced by joining at least two nucleic acid sequences together in such a manner that the fragment is expressed as a protective fusion protein containing at least two functionally equivalent protective proteins capable of protecting animals from disease caused by at least one infectious agent. Examples of fusion fragments of the present invention include an antigenic foot and mouth viral protein (e.g., VP1) joined to P30, a hepatitis viral protein joined to P30, and an antigenic human immunodeficiency viral protein joined to P30.

As heretofore stated, a recombinant molecule of the present invention includes a nucleic acid sequence of the present invention operatively linked to an alphavirus expression vector that is packaging-defective (i.e., not able to effect packaging of the recombinant molecule into a virus) but that is capable of directing transcription of genes contained in the recombinant molecule, herein referred to as a "packaging-defective alphavirus expression vector", or simply as an "alphavirus expression vector." As used herein, the phrase "capable of directing transcription of said recombinant molecule" refers to the ability of the alphavirus expression vector, when placed in an appropriate host, to use the host machinery as well as its own signals and/or encoded enzymes to effect transcription of genes present on the recombinant molecule including the nucleic acid sequence to which the expression vector is operatively linked. As used herein, the phrases "packaging-defective" and "not capable of effecting packaging of said recombinant molecule" each refers to the inability of the alphavirus expression vector alone to accomplish packaging of the recombinant molecule into a virus since the alphavirus expression vector does not contain a complete copy of the genes that encode the structural polypeptides that make up the viral coat. Preferred alphavirus expression vectors (i.e., packaging-defective alphavirus expression vectors) of the present invention retain the site required for packaging within nsP1 but lack the ability to produce one or more functional alphavirus structural polypeptides required to effect packaging of the recombinant molecule. The size of alphavirus expression vectors of the present invention is a function of the size of the recombinant molecules that contain the vectors since the recombinant molecules must be of a size appropriate to be packaged into viral particle vaccines according to the method described below.

An alphavirus expression vector of the present invention is preferably able to direct replication of the recombinant molecule, meaning that when the recombinant molecule is placed in an appropriate host cell, the alphavirus expression vector is able to the use the host cell machinery as well as its own signals and/or encoded enzymes to effect replication of the recombinant molecule. In a preferred embodiment, the recombinant molecule contains genes encoding each of the alphavirus nonstructural polypeptides (e.g., nonstructural polypeptides nsP1, nsP2, nsP3, and nsP4), or functional equivalents thereof, and other signals required for transcription and replication of the recombinant molecule, but lacks the ability to produce one or more functional structural polypeptides (e.g., capsid polypeptide C or envelope glycopolypeptides E1 or E2), which may be due to lack of a gene encoding the protein and/or mutation of the gene such that a functional polypeptide cannot be produced. Such a recombinant molecule is able to be transcribed and replicated within a cell but cannot be packaged into an infectious virus unless a helper virus is present.

An alphavirus expression vector of the present invention can comprise any alphavirus expression vector and can be a hybrid between at least two alphaviruses. As used herein, a "hybrid" alphavirus expression vector is an expression vector that contains different segments from different alphaviruses. Preferred alphavirus expression vectors include Sindbis virus expression vectors, Semliki Forest virus expression vectors, Ross River virus expression vectors, and hybrids thereof. Sindbis virus expression vectors are particularly preferred alphavirus expression vectors despite a statement by Liljestrom et al., ibid., that technical difficulties (e.g., low transfection rates) have precluded wide spread use of Sindbis virus vectors. According to the present invention, either lipofection or electroporation permits straightforward manipulation of Sindbis virus vectors.

Sindbis virus vectors are preferred because, unlike Semliki Forest virus and other alphaviruses, Sindbis virus is not associated with human disease. In addition, Sindbis virus has a wide host range. For example, Sindbis virus can infect a number of organisms including mammalian, avian, insect, amphibian, and reptilian cells. Sindbis virus has infected all cell types studied so far, including, but not limited to, Chinese hamster ovary cells, baby hamster kidney cells, quail (e.g., QT-6) cells, chicken embryo fibroblasts, human tumor cells, mosquito and Drosophila cells. Sindbis virus can also be transmitted to vertebrate hosts, such as birds or mammals, by mosquitos. Sindbis virus gene expression, which occurs in the cytoplasm of the cell, is quite efficient, rapid, and can be modulated. For example, Xiong et al., ibid., reported the production of up to $1 \times 10^8$ molecules of chloramphenicol acetyltransferase (CAT) per cell transfected with Sindbis virus expression vectors operatively linked to CAT gene in less than about 20 hr. The authors also reported that use of a replication temperature sensitive Sindbis virus vector led to modulated expression of CAT.

An alphavirus expression vector of the present invention preferably contains an alphavirus subgenomic promoter which, in natural alphavirus isolates, controls expression of viral structural polypeptide genes. In a preferred embodiment, at least one of the structural polypeptide genes of a natural alphavirus vector is deleted and a nucleic acid sequence of the present invention is joined to the vector such that expression of the nucleic acid sequence is under the control of alphavirus subgenomic promoter. Alphavirus subgenomic promoters are advantageous because they lead to high levels of protein production in relatively short periods of time. However, it should be appreciated that other suitable promoters may also be used to control expression of a protective protein of the present invention. Suitable alphavirus subgenomic promoters of the present invention include any alphavirus subgenomic promoter including hybrids thereof. A hybrid alphavirus subgenomic promoter contains different segments from different alphaviruses. Preferred subgenomic promoters include subgenomic promoters of Sindbis virus, Semliki Forest virus, Ross River virus, Middleburg virus, O'Nyong-nyong virus, Eastern equine encephalitis virus, Western equine encephalitis virus, Venezuelan equine encephalitis virus, and hybrids thereof. More preferred alphavirus subgenomic promoters include Sindbis virus subgenomic promoters, Semliki Forest virus subgenomic promoters, Ross River virus subgenomic promoters, and hybrids thereof, with Sindbis virus subgenomic promoters being even more preferred.

Figure 5:
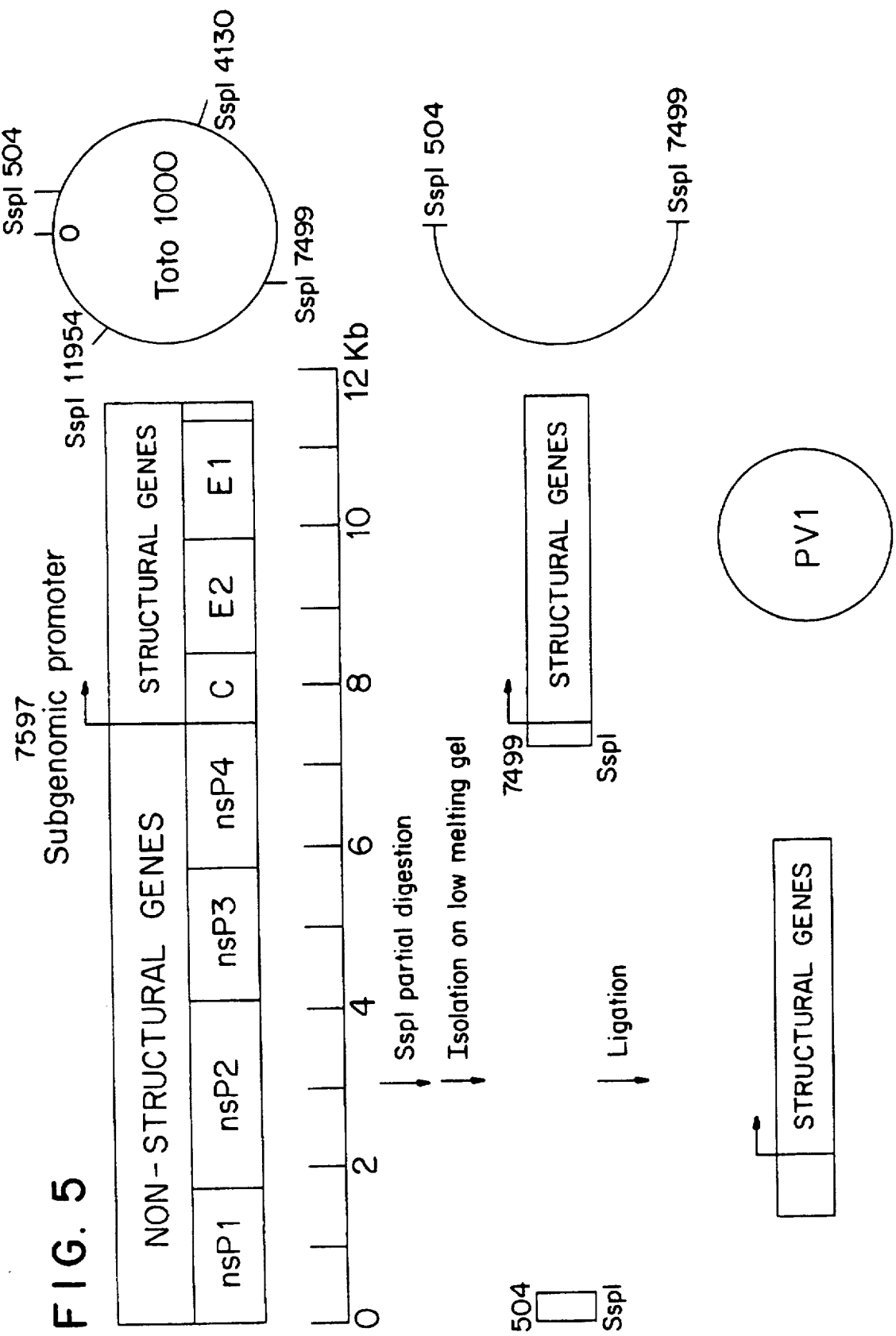

Particularly preferred Sindbis virus expression vectors include SV1 and SV2, which are depicted in FIG. 5. SV1 contains all the genes encoding nonstructural Sindbis virus polypeptides, the subgenomic promoter plus 14 nucleotides downstream from the subgenomic RNA initiation site, and 616 nucleotides at the 3' end of the Sindbis viral genome plus the poly(A) tail. SV2 is similar to SV1 except that SV2 contains only 62 nucleotides of the 3' end of the Sindbis viral genome, thereby permitting the insertion of a larger nucleic acid sequence. Each of these vectors has a site for insertion of a nucleic acid sequence of the present invention as indicated.

In accordance with one embodiment of the present invention, a recombinant molecule is produced by (a) isolating a nucleic acid sequence that encodes a protective protein, (b) isolating a packaging-defective alphavirus expression vector capable of directing transcription of a recombinant molecule of which the vector is a part, and (c) operatively linking the nucleic acid sequence to the expression vector to obtain a recombinant molecule in which expression of the nucleic acid sequence is controlled by the expression vector. Preferably, the expression vector is also capable of directing replication of the recombinant molecule. For example, a recombinant molecule can be produced by (a) isolating a nucleic acid sequence that encodes a natural or functionally equivalent *Toxoplasma gondii* P30 protein capable of protecting an animal from toxoplasmosis; (b) isolating a Sindbis virus expression vector that contains a subgenomic promoter and that encodes each of the Sindbis virus nonstructural polypeptides, but that is unable to encode at least one functional Sindbis virus structural polypeptide; and (c) operatively linking the P30 sequence to the subgenomic promoter so that expression of P30 is controlled by the subgenomic promoter. In one embodiment, at least one of the genes encoding Sindbis virus structural polypeptides C, E1, or E2 is replaced by the sequence encoding a P30 antigen.

Techniques for isolating nucleic acid sequences and expression vectors and for operatively linking a coding sequence to an expression vector are described in detail in Sambrook et al., ibid. Since it is technically difficult to perform recombinant techniques on RNA viruses, the RNA alphavirus vectors of the present invention are preferably converted into double-stranded cDNA copies using standard techniques. After genetic manipulations, such as the insertion of a nucleic acid sequence of the present invention into an alphavirus expression vector, the resultant DNA recombinant molecule can be transcribed into an RNA recombinant molecule, for example, by the following method: The DNA recombinant molecule is inserted into a plasmid containing an RNA polymerase promoter and is transcribed in vitro in the presence of an appropriate RNA polymerase and other reagents to effect transcription. These techniques are described in greater detail in Sambrook et al., ibid., and Xiong et al., ibid. Suitable RNA polymerase promoters include, but are not limited, to bacteriophage SP6, T7 and T3 promoters. A preferred RNA polymerase promoter is the bacteriophage SP6 promoter (e.g., Melton et al., pp. 7035–7056, 1984, *Nucleic Acids Research*, Vol. 12). The DNA recombinant molecule to be transcribed is preferably a linear or supercoiled molecule, with linear being more preferred.

Preferred recombinant molecules of the present invention include alphavirus expression vectors operatively linked to preferred nucleic acid sequences of the present invention. Particularly preferred recombinant molecules of the present invention include SV1:nP30.1008, SV1:nP30.924, SV1:nP30.873, SV1:nP30.789, SV1:nP30.771, SV1:nP30.924SS, SV1:nP30.867SS, SV1:nP30.783SS, SV1:nP30.771SS, SV2:nP30.1008, SV2:nP30.924, SV2:nP30.873, SV2:nP30.789, SV2:nP30.771, SV2:nP30.924SS, SV2:nP30.867SS, SV2:nP30.783SS, and SV2:nP30.771SS. The name of each of these particularly preferred recombinant molecules indicates the alphavirus expression vector (e.g., SV1) to which the nucleic acid sequence (e.g., nP30.1008) is operatively linked (:).

In accordance with the present invention, a recombinant virus particle vaccine can be produced by a method which includes the steps of (a) co-transfecting a host cell with a recombinant molecule and an alphavirus packaging vector; (b) culturing the transfected cell in an effective medium to produce a recombinant virus particle; (c) recovering the particle; and (d) formulating a vaccine therefrom. Preferably, the vaccine comprises a recombinant molecule packaged in a viral coat that includes alphavirus structural polypeptides such as capsid polypeptide (C) and two envelope glycopolypeptides (E1 and E2). While not being bound by theory, it is believed that the recombinant molecule complexes with the capsid polypeptide to form an intracellular icosahedral nucleocapsid which interacts with the cytoplasmic domains of the transmembrane envelope polypeptides E1 and E2, resulting in the budding of the virus vaccine at the plasma membrane.

Since the recombinant molecules of the present invention do not themselves encode all the polypeptides required for packaging, the components of the viral coat can be provided by co-transfecting a host cell with both a recombinant molecule and an alphavirus packaging vector which acts as a helper virus to package the recombinant molecule. As used herein, "an alphavirus packaging vector" is an alphavirus-based vector that contains the genes that encode the structural polypeptides required for packaging of the recombinant molecule into a virus particle. The packaging vector also contains sequences corresponding to the 5' and 3' ends of alphavirus RNA molecules which are important in transcription and replication. However, the alphavirus packaging vector is unable to direct its own packaging (i.e., self-package) because it lacks the site located within the nsP1 gene thought to be necessary for packaging to occur. As such, packaging vectors of the present invention are much more useful for packaging recombinant molecules than are viral genomes containing the entire alphavirus RNA molecule since co-transfection of a host cell with a recombinant molecule and a packaging vector of the present invention results in the desired recombinant virus particle vaccine but does not lead to the production of infectious alphaviruses (i.e., alphaviruses which are able to replicate and package themselves).

Figure 6:
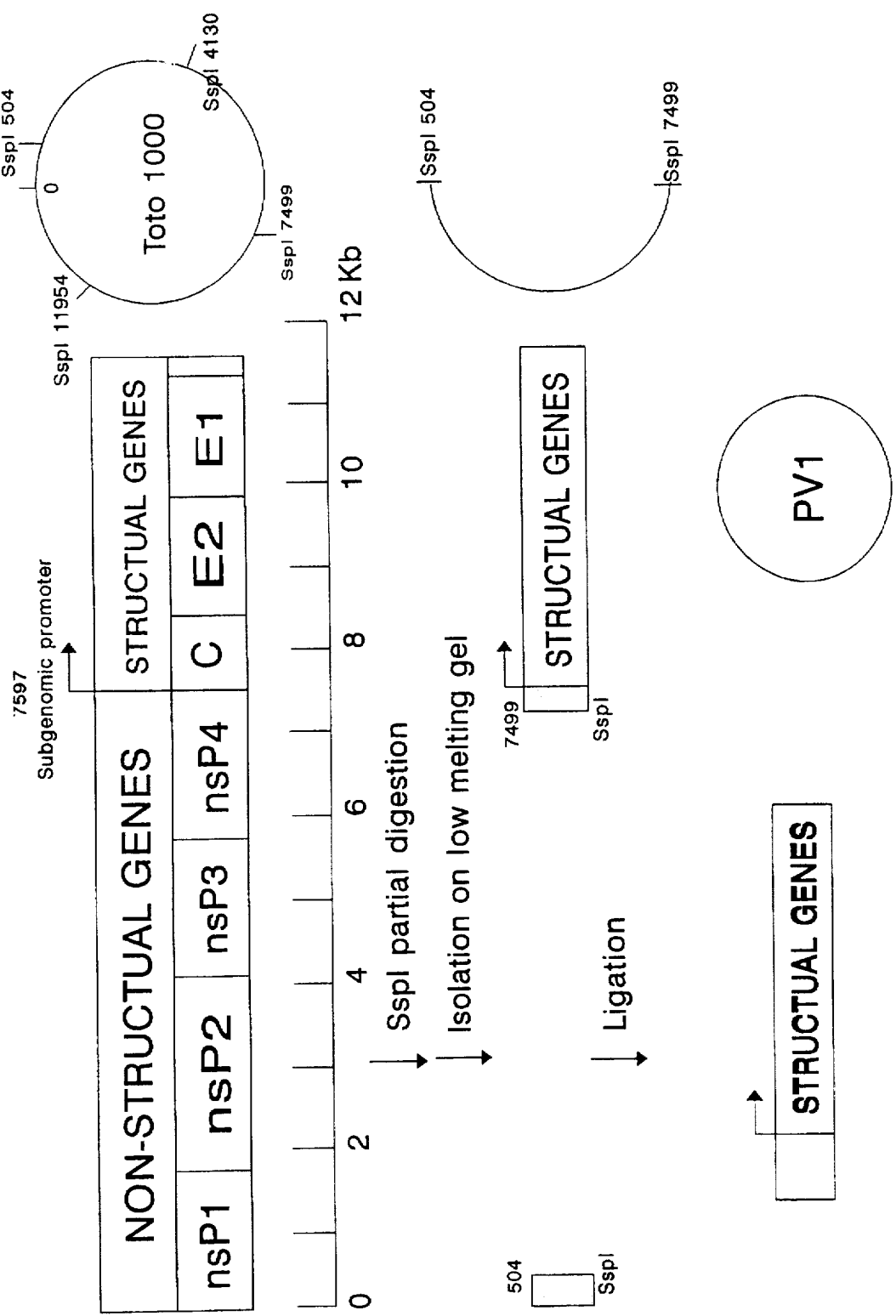

Suitable alphavirus packaging vectors include Sindbis virus packaging vectors, Semliki Forest virus packaging vectors, and Ross River virus packaging vectors. Sindbis virus packaging vectors are preferred, particularly those that contain a minimal amount of genetic information to effect packaging. While not being bound by theory, it is believed that smaller packaging vectors are better because they are more efficient and more RNA can be produced per unit time. Particularly preferred packaging vectors are Sindbis virus packaging vectors that contain the structural polypeptide genes under the control of the subgenomic promoter and also contain replication and transcription signals at the 5' and 3' ends of Sindbis viral RNA. A particularly preferred Sindbis virus packaging vector is PV1, the production of which is depicted in FIG. 6.

According to the present invention, a recombinant virus particle vaccine can also be produced by (a) introducing, by transfection, a recombinant molecule into a host cell that already contains genes integrated into its chromosomal DNA and/or on extrachromosomal vectors that encode the structural polypeptides required to effect packaging of the recombinant molecule (i.e., a host cell that is capable of packaging the recombinant molecule into a virus particle); (b) culturing the transfected cell in an effective medium to produce the virus particle; (c) recovering the virus particle; and (d) formulating a vaccine therefrom. Preferred genes are structural polypeptide genes of Sindbis virus, Semliki Forest virus, or Ross River virus, with the structural polypeptide genes of Sindbis virus being more preferred. For example, Chinese hamster ovary cells containing genes encoding alphavirus structural polypeptides C, E1, E2, E3, and 6K, or functional equivalents thereof of said polypeptides can be used as host cells.

A number of host cells are suitable for recombinant virus particle vaccine production since alphaviruses have such wide host ranges. Suitable host cells include, but are not limited to, mammalian, insect, avian, reptilian, amphibian, and some insect (e.g., mosquito and Drosophila) cells. Preferred host cells include mammalian, insect, and avian cells. More preferred host cells include Chinese hamster ovary cells, baby hamster kidney cells, chicken embryonic fibroblasts, and mosquitos.

As used herein, transfection includes any means for introducing a nucleic acid sequence, expression vector, recombinant molecule, or packaging vector, into a host cell, including, but not limited to transformation, electroporation, microinjection, lipofection, adsorption, and protoplast fusion. Preferred transfection techniques are lipofection and electroporation.

After transfection, transfected cells are cultured in an effective medium, using techniques such as those described in Xiong et al., ibid. As used herein, an effective medium refers to any medium in which the transfected cells can produce recombinant virus particle vaccines. An effective medium is typically an aqueous medium comprising assimilable carbohydrate, nitrogen and phosphate sources, as well as appropriate salts, minerals, metals and other nutrients, such as vitamins and hormones. Culturing is carried out at a temperature, pH and oxygen content appropriate for the transfected cell. Such culturing conditions are well within the expertise of one of ordinary skill in the art. Examples of preferred effective media are included in the Examples section.

Recombinant virus particles can be recovered from the cultured transfected cells using a combination of standard techniques such as, but not limited to, affinity chromatography, ion exchange chromatography, filtration, and hydrophobic interaction chromatography. A preferred recovery technique is Matrex® Cellufine™ Sulfate Media & Virus Recovery System, available from Amicon Inc., Danvers, Mass.

Due to the nature of the recombinant molecules and packaging vectors of the present invention, essentially no infectious virus is formed (i.e., the probability of forming infectious virus is less than about $1 \times 10^{-6}$), thus simplifying recovery of recombinant virus particle vaccines. Sindbis virus recombinant molecules and packaging vectors are particularly preferred since, even if a small amount of infectious Sindbis virus is produced, the virus is safe.

Preferably, a recombinant virus particle of the present invention is recovered in "substantially pure" form. As used herein, "substantially pure" refers to a purity that allows for the effective use of the recombinant virus particle as a vaccine without substantial negative side effects. One embodiment of a substantially pure virus particle is a cell lysate containing the virus particle that generates substantially no side effects when administered to an animal in an effective amount to protect the animal from disease. It is within the scope of the present invention to recover recombinant virus particles having a purity of up to and including about 99 percent.

A recombinant virus particle vaccine of the present invention, when administered to an animal in an effective amount, infects the cells of the animal (in a manner essentially harmless to the animal) and directs the production of a protective protein able to protect the animal from an infectious or metabolic disease. Preferred recombinant virus particle vaccines are those that protect animals from diseases caused by protozoan parasites, helminth parasites, ectoparasites, fungi, bacteria and viruses. More preferred recombinant virus particle vaccines are those that protect animals from infectious agents such as protozoan parasites, helminth parasites, or ectoparasites, including parasites of the genera Toxoplasma, Dirofilaria, Cryptosporidium, Eimeria, Neospora, Isospora, Plasmodium, Babesia, Theileria, Hepatozoon, Encephalitozoon, Nosema, Pneumocystis, Cryptococcus, Candida, and Histoplasma, and even more preferably *Toxoplasma gondii*, *Dirofilaria immitis*, or Cryptosporidium.

A preferred recombinant virus particle vaccine of the present invention includes a recombinant molecule packaged in a Sindbis virus coat in which the recombinant molecule contains a nucleic acid sequence encoding a *Toxoplasma gondii* antigen capable of protecting an animal from toxoplasmosis operatively linked to a Sindbis virus expression vector. More preferred recombinant virus particle vaccines (VPVs) include: VPV SV1:nP30.1008, VPV SV1:nP30.924, VPV SV1:nP30.873, VPV SV1:nP30.789, VPV SV1:nP30.771, VPV SV1:nP30.924SS, VPV SV1:nP30.867SS, VPV SV1:nP30.783SS, VPV SV1:nP30.771SS, VPV SV2:nP30.1008, VPV SV2:nP30.924, VPV SV2:nP30.873, VPV SV2:nP30.789, VPV SV2:nP30.771, VPV SV2:nP30.924SS, VPV SV2:nP30.867SS, VPV SV2:nP30.783SS, and VPV SV2:nP30.771SS. Each of these vaccines includes the designated recombinant molecule packaged in a Sindbis virus coat. For example, vaccine VPV SV1:nP30.1008 includes recombinant molecule SV1:nP30.1008 packaged in a Sindbis virus coat; recombinant molecule SV1:nP30.1008 contains a nucleic acid sequence that encodes a *Toxoplasma gondii* P30 antigen of 336 amino acids that is operatively linked to alphavirus expression vector SV1.

Recombinant virus particle vaccines of the present invention can be used to protect animals from a variety of diseases, including infectious and metabolic diseases. When administered to an animal, the recombinant virus particle vaccine infects cells within the immunized animal and directs the production of a protective protein or RNA that is capable of protecting an animal from disease. For example, a *Toxoplasma gondii* antigen will protect an animal from toxoplasmosis, a feline or human immunodeficiency virus (FIV or HIV, respectively) antigen will protect an animal from FIV or HIV infection, a *Dirofilaria immitis* antigen will protect an animal from heartworm, a Coccidia antigen will protect an animal from coccidiosis, a *Plasmodium falciparum* antigen will protect an animal from malaria, a Cryptosporidium antigen will protect an animal from enteric disease, an *Encephalitozoon cuniculi* antigen will protect an animal from encephalitozoonosis, and a Pneumocystis antigen will protect an animal from pneumonia.

Vaccines of the present invention can be administered to any animal, preferably to mammals, birds and insects, and more preferably to humans, dogs, cats, sheep, pigs, cattle, horses, poultry, and other pets and/or economic food animals. A preferred vaccine is one that, when administered to an animal, is preferably able to elicit (i.e., stimulate) the production of very high antibody titers as well as a high-level cellular immune response to the protective protein encoded by the nucleic acid sequence. Administration of a vaccine containing multiple nucleic acid sequences targeting multiple infectious agents can protect the vaccinated animal from those multiple infectious diseases.

Vaccines can be formulated in an aqueous balanced salt solution that the animal to be vaccinated can tolerate. In one embodiment of the present invention, the vaccine can also include an immunopotentiator, such as an adjuvant or a carrier. One advantage of live virus-based vaccines, such as the recombinant virus particle vaccines of the present invention, is that adjuvants and carriers are not required to produce an efficacious vaccine. However, it should be noted that use of immunopotentiators is not precluded by the present invention.

Adjuvants are typically substances that generally enhance the immune response of an animal to a specific antigen. Suitable adjuvants include, but are not limited to, Freund's adjuvant, aluminum-based salts, calcium-based salts, silica, polynucleotides, coat proteins from other viruses, bacterial-derived preparations, gamma interferon, Ribi adjuvants (available from Ribi ImmunoChem Research, Inc., Hamilton, Mont.), and saponins and their derivatives, such as Quil A (available from Superfos Biosector A/S, Denmark).

Carriers are typically compounds that increase the half-life of a vaccine in a vaccinated animal. Suitable carriers include, but are not limited to, polymeric controlled release formulations, biodegradable implants, liposomes, bacteria, other viruses, oils, esters, and glycols.

In order to protect animals from a disease, a recombinant virus particle vaccine of the present invention is administered in an effective amount, wherein an "effective amount" is an amount that allows the animal to produce sufficient protective protein or RNA to protect itself from the disease. For example, when the protective protein is a $Toxoplasma$ $gondii$ antigen, the recombinant virus particle vaccine is administered according to a protocol that results in the animal producing a sufficient immune response to protect itself from toxoplasmosis. The administration protocol includes individual dose size, number of doses, frequency of dose administration, and mode of administration. A suitable single dose of the vaccine is a dose that is capable of protecting an animal from a disease when administered one or more times over a suitable time period. A preferred single dose of the vaccine is from about $1 \times 10^4$ to about $1 \times 10^5$ virus plaque forming units (pfu) per kilogram (kg) body weight of the animal. Booster vaccinations can be administered from about 2 weeks to several years after the original vaccination. Preferably booster vaccinations are administered when the immune response of the animal becomes insufficient to protect the animal from disease. A preferred administration schedule is one in which from about $1 \times 10^4$ to about $1 \times 10^5$ virus plaque forming units per kilogram (kg) body weight of the animal are administered from about 1 to about 2 times over a time period of from about 12 to about 18 months. Modes of administration can include, but are not limited to, subcutaneous, intradermal, intravenous, nasal, oral, transdermal and intramuscular routes.

The efficacy of a recombinant virus particle vaccine of the present invention to protect an animal from disease can be tested in a variety of ways including, but not limited to, detection of protective protein or RNA within the vaccinated animal or challenge of the vaccinated animal with an appropriate infectious agent to determine whether the animal is now resistant to the disease caused by such an agent. When the protective protein is an immunogen, it is also possible to determine vaccine efficacy by measuring antibody production by the animal in response to the immunogen (using either the immunogen or corresponding infectious agent as the target) and/or determining the ability of immune response cells (e.g. splenocytes) to respond to the infectious agent at various effector:target ratios.

One method to determine the ability of a nucleic acid of the present invention to encode a protective protein capable of eliciting an immune response against a disease, such as toxoplasmosis, is as follows. A recombinant molecule of the present invention is transfected into a host cell, preferably into a mammalian, insect, or avian cell. The host cell is cultured under conditions that promote production of the protective protein (e.g., a P30 antigen), which subsequently can be recovered from the culture. The recovered protective protein is then injected one or more times into an animal, such as a rabbit, in a manner to promote the production of antibodies against the protective protein. Serum from the rabbit is subsequently recovered and tested for its ability to bind to, for example, the recovered protective protein, the corresponding native protective protein, and the corresponding infectious agent, with affinities that suggest that the nucleic acid encodes a suitable immunogen. For example, in the case of a $Toxoplasma$ $gondii$ P30 antigen, the serum is tested against recovered P30 antigen, native $Toxoplasma$ $gondii$ P30 antigen, and $Toxoplasma$ $gondii$ tachyzoite parasites.

In one embodiment of the present invention, a recombinant virus particle vaccine, preferably one encoding a $Toxoplasma$ $gondii$ antigen, and more preferably VPV SV1:nP30.1008 is administered subcutaneously to an animal, preferably a mammal, one or more times over a time period of from about 2 to about 4 weeks. Vaccine efficacy can be measured, for example, by determining whether the serum of the vaccinated animal contains antibodies that react with either a $Toxoplasma$ $gondii$ parasite or the $Toxoplasma$ $gondii$ antigen encoded by the nucleic acid sequence in the vaccine and/or, preferably, by challenging the animal with a dose of $Toxoplasma$ $gondii$ parasites and determining if the animal develops toxoplasmosis. Protection can be monitored, for example, by mortality or by assaying for brain cysts.

In accordance with one embodiment of the present invention, the efficacy of a vaccine of the present invention may be improved by co-administering the recombinant virus particle vaccine with a protective protein encoded by the nucleic acid sequence of the recombinant virus particle vaccine. While not being bound by theory, it is believed that administration of a protective protein in conjunction with the recombinant virus particle may boost particularly the antibody titer. The protective protein can be administered prior to, concomitant with, and/or following administration of the recombinant virus particle vaccine. The protective protein can be either native (naturally-occurring), synthetic, or recombinant. The protective protein can be a natural protein or functional equivalent thereof. The protective protein should be sufficiently pure to allow for effective use of the protective protein as a vaccine; i.e., it does not cause substantial side effects. The protective protein can be joined (i.e., conjugated) to a carrier or other material that enhances the immunogenicity of the protective protein.

In one embodiment, a recombinant virus particle vaccine containing a nucleic acid sequence encoding a $Toxoplasma$ $gondii$ P30 antigen is administered with a sufficiently pure $Toxoplasma$ $gondii$ P30 antigen, such as, but not limited to, a native P30 antigen (Khan et al., ibid., Bulow et al., ibid.), a recombinant P30 antigen such as P30.336, P30.308, P30.291, P30.289, P30.263, P30.261, P30.257, or a fusion protein between a recombinant P30 antigen and a fusion segment, such as a fusion segment that aids in protein purification (e.g., glutathione-S-transferase), such as GST-P30.257 encoded by nucleic acid sequence nGST-nP30.771.

The following experimental results are provided for purposes of illustration and are not intended to limit the scope of the invention.

EXAMPLES

Example 1

Production of nucleic acid sequences encoding recombinant P30 antigens

A. An approximately 1020 base pair DNA fragment, called nP30.1008, shown in FIG. 4, containing the entire coding region for the *Toxoplasma gondii* P30 antigen (about 336 amino acids, assuming that the translation initiation site is as shown in FIG. 2) and flanked by SmaI and XbaI restriction endonuclease sites immediately adjacent to the translation initiation (start) site and XhoI, KpnI, and MluI restriction endonuclease sites immediately adjacent to the translation termination (stop) site was copied from a clone (Burg et al., ibid.) containing the P30 gene with natural flanking sequence using polymerase chain reaction (PCR) amplification (Sambrook et al., ibid.). The specific primers used in the amplification reaction were:

```
Primer #1 (SEQ ID NO: 2)
5' CCCGGGTCTA GA   ATG  TCG GTT TCG CTG CAC CAC    3'
   SmaI   XbaI     1st  ATG at amino terminus of P30
Primer #2 (SEQ IF NO: 3)
5' ACGCGTGGTA CCTCGAG  TCA CGC GAC ACA AGC T       3'
   MluI    KpnI  XhoI  Translation Stop Site
```

The nucleic acid sequence nP30.1008 was recovered, restricted with XbaI and XhoI, and inserted into plasmid pBluescript II (a cloning vector available from Stratagene, San Diego, Calif.) which had also been restricted with XbaI and XhoI. The resulting vector, referred to as pB:nP30.1008, encodes *Toxoplasma gondii* antigen P30.336.

B. A nucleic acid sequence encoding a functionally equivalent P30 antigen, lacking both amino and carboxyl terminal hydrophobic residues, was produced by the following method. A fragment of about 800 base pairs was copied by PCR amplification of a portion of bP:nP30.1008 (produced as described in Example 1A) using the following primers:

```
Primer #3 (SEQ ID NO: 4)
5'  GTCGACCCCG GGTCTAGACC ATG GCA TCG GAT CCC CC 3'
    SalI    SmaI    XbaI    NcoI
                            Translation Start Site
Primer #4 (SEQ ID NO: 5)
5'  ACGCGTGGTA CCTCGAG  TTA TGC TGA CCC TGC AGC CCC GGC
          KpnI   XhoI   Translation Stop Site
```

The amplified nucleic acid sequence, denoted nP30.789, is shown in FIG. 4. nP30.789 encodes P30.263, a protective protein, the primary translation product of which is about 263 amino acids, spanning amino acid from about 46 through amino acid about 308, as numbered in FIG. 2. As such, about 45 amino acid residues have been removed from the amino terminus and about 28 amino acid residues have been removed from the carboxyl terminus of P30.336.

C. A nucleic acid sequence encoding a functionally equivalent P30 antigen, lacking amino terminal hydrophobic residues, is produced by the following method. A fragment of about 880 base pairs is copied by PCR amplification of a portion of bP:nP30.1008 (produced as described in Example 1A) using primer #3 (SEQ ID NO:4) (described in Example 1B) and primer #2 (SEQ ID NO:3) (described in Example 1A). The amplified nucleic acid sequence, called nP30.873, is shown in FIG. 4. nP30.873 encodes P30.291, a protective protein, the primary translation production of which is about 291 amino acids, spanning amino acid from about 46 through amino acid about 336, as numbered in FIG. 2. As such, about 45 amino acid residues are removed from the amino terminus of P30.336.

D. Another nucleic acid sequence encoding a functionally equivalent P30 antigen, lacking amino terminal hydrophobic residues, was produced by the following method. A fragment of about 880 base pairs was copied by PCR amplification of a portion of bP:nP30.1008 (produced as described in Example 1A) using the following primers:

```
Primer #5 (SEQ ID NO: 6)
5'  GTCGACTCTA GACCCGGG ATG GCA TCG GAT CCC CC  3'
                SmaI    Translation Start Site
Primer #6 (SEQ ID NO: 7)
5'  ACGCGTGGTA CCGAATTC TCA CGC GAC ACA AGC T  3'
                EcoRI   Translation Stop Site
```

This amplified nP30.873 nucleic acid sequence is similar to the nP30.873 nucleic acid sequence shown in FIG. 4 except that this nucleic acid sequence is flanked by SmaI and EcoRI restriction sites rather than by XbaI and XhoI restriction sites.

E. A nucleic acid sequence encoding a functionally equivalent P30 antigen, lacking carboxyl terminal hydrophobic residues, is produced by the following method. A fragment of about 940 base pairs is copied by PCR amplification from bP:nP30.1008 (produced as described in Example 1A) using primer #1 (SEQ ID NO:2) (described in Example 1A) and primer #4 (SEQ ID NO:5) (described in Example 1B). The amplified nucleic acid sequence, called nP30.924, is shown in FIG. 4. nP30.924 encodes P30.308, a protective protein, the primary translation product of which is about 308 amino acids, spanning amino acid from about 1 through amino acid about 308, as numbered in FIG. 2. As such, about 28 amino acid residues are removed from the carboxyl terminus of P30.336.

F. A nucleic acid sequence encoding a functionally equivalent P30 antigen, lacking both amino and carboxyl terminal hydrophobic residues, but having a signal sequence in its primary translation product is produced in the following manner. A fragment of about 783 base pairs is produced by PCR amplification of a portion of bP:nP30.1008 (produced as described in Example 1A) using primer #7 (SEQ ID NO:8) and primer #4 (SEQ ID NO:5) (described in Example 1B). Primer #7, (SEQ ID NO:8) shown below, contains a nucleic acid signal segment encoding the first about 23 residues of human t-PA joined to a nucleotide sequence encoding amino acid residues about 48 through about 54 of P30.336.

```
Primer #7 (SEQ ID NO: 8)
5' GTCGACCCCG GGTCTAGAC ATG GAT GCA ATG AAG AGA GGG
                 XbaI        Translation Start of t-PA
   CTC TGC TGT GTG CTG CTA CTG TGT GGA GCA GTC TTC GTT
   TCG CCC TCG GAT CCC CCT CTT GTT GCC 3'
            P30 Sequences
```

The amplified nucleic acid sequence, called nP30.783SS, encodes P30.261SS, a protective protein, the primary translation product of which is about 283 amino acids. P30.261SS is capable of being secreted as a protein, which upon secretion from the cell is very similar to P30.263 except that P30.261SS begins at amino acid 48 of P30 as numbered in FIG. 2, whereas P30.263 begins at amino acid 46. Amino acid 48 is thought to be the amino-terminal amino acid of the mature P30 protein (Burg et al., ibid.).

G. A nucleic acid sequence which encodes a fusion segment (i.e., glutathione S-transferase, or GST) joined to a *Toxoplasma gondii* antigen lacking a majority of amino and carboxyl terminal hydrophobic sequences was produced in the following manner.

P30.5 COS1.1 DNA, a clone containing the entire *Toxoplasma gondii* antigen gene (Burg et al., ibid) was digested with BamHI and PstI in order to obtain a BamHI/PstI fragment of about 771 base pairs which encodes P30 antigen containing amino acid residues spanning from about 49 through about 305, as numbered in FIG. 2. The BamHI/PstI fragment was inserted into plasmid pBluescript II (available from Stratagene, San Diego, Calif.) which had also been digested with BamHI and PstI. The resulting vector, referred to as pB:nP30.771, encodes *Toxoplasma gondii* antigen P30.257. Vector pB:nP30.771 was digested with BamHI and EcoRI to obtain a BamHI/EcoRI fragment of about 773 base pairs that was subsequently inserted into the GST fusion vector pGEX-1 (Smith et al., pp. 31–40, 1988, *Gene*, Vol. 67) which had also been digested with BamHI and EcoRI. The resultant vector, denoted pGEX:nP30.771, contained the nP30.771 coding region immediately adjacent to and in the same reading frame as the GST gene, the transcription of which was under the control of the tac promoter.

A nucleic acid sequence of about 703 base pairs containing the GST coding region joined to the nP30.771 coding region, called nGST-nP30.771, was produced by PCR amplification of a portion of the pGEX:nP30.771 vector using the primers shown below:

```
Primer #8 (SEQ ID NO: 9)
5' GTCGACCCCG GG TCTAGACC ATG TCC CCT ATA GG 3'
                  XbaI     Translation Start Site
Primer #9 (SEQ ID NO: 10)
5' ACGCGTGGTA CCTCGAG TCA G TCA G TCA CGATG 3'
                XhoI   Translation Stop Sites
```

As indicated, primer #8 (SEQ ID NO:9) spans the GST translation start site of pGEX-1, and primer #9 (SEQ ID NO:10) spans the three translation stop sites in pGEX-1. The amplified nucleic acid sequence nGST-nP30.771 encodes a GST fusion protein in which GST is joined to a P30 protein of about 257 amino acids, the P30 protein lacking the initial about 48 amino acids and the terminal about 31 amino acids of P30.336.

Example 2

Production of a recombinant molecule containing a nucleic acid sequence encoding a P30 antigen A recombinant molecule containing a nucleic acid sequence encoding a full-length *Toxoplasma gondii* P30 antigen is produced by the following method.

Sindbis virus expression vector TRCAT62 (see Xiong et al., ibid.) is a double-stranded DNA expression vector which contains (a) the genes encoding nonstructural Sindbis virus polypeptides nsP1, nsP2, nsP3, and nsP4, (b) the subgenomic promoter plus 14 nucleotides downstream from the subgenomic RNA initiation site which is ligated to a gene encoding chloramphenicol acetyltransferase (CAT), (c) 62 nucleotides at the 3' end of the Sindbis viral genome plus the poly(A) tail, and (d) at bacteriophage SP6 promoter immediately upstream of the Sindbis virus nonstructural genes. The gene encoding CAT is flanked by an XbaI restriction site at its 5'end and an XhoI restriction site at its 3'end.

Double stranded DNA recombinant molecule dSV2:nP30.1008 is produced in the following manner.

TRCAT62 is digested with the restriction enzymes XbaI and XhoI, thereby removing the CAT gene and forming dSV2 (see FIG. 5). Nucleic acid sequence nP30.1008 (produced as described in Example 1A and shown in FIG. 4) is digested with XbaI and XhoI and subsequently ligated into dSV2 to form DNA recombinant molecule dSV2:nP30.1008.

RNA recombinant molecule SV2:nP30.1008 is produced from dSV2:nP30.1008 by digesting dSV2:nP30.1008 DNA with restriction enzyme MluI and incubating the digested DNA with bacteriophage SP6 RNA polymerase under conditions similar to those described by Xiong et al., ibid., and Rice et al., *J. Virology* 61, 3809–3819, 1987, in order to produce run-off transcripts comprising SV2:nP30.1008. Trace quantities of $^3$H-UTP (uridine triphosphate) or $\alpha$-$^{32}$p-CTP (cytosine triphosphate) are included in the transcription reaction to permit quantitation (i.e., using DE81 filter paper, available from Whatman Inc., Clifton, N.J.) and gel analysis of the RNA transcripts.

A number of other RNA recombinant molecules can be produced as described above, including SV2:nP30.924, SV2:nP30.873, SV2:nP30.789, SV2:nP30.924SS, SV2:nP30.867SS, and SV2:nP30.783SS, SV1:nP30.1008, SV1:nP30.924, SV1:nP30.873, SV1:nP30.789, SV1:nP30.924SS, SV1:nP30.867SS, and SV1:nP30.783SS.

Example 3

Production of Sindbis virus packaging vector

The following method is used to produce a Sindbis virus packaging vector which contains the genetic information to encode Sindbis virus structural polypeptides and control signals for replication and transcription but which does not contain the site thought to be required for packaging, which is located within the nsP1 gene. Therefore, the packaging vector cannot effect self-packaging.

A full-length cDNA copy of Sindbis virus vector Toto1000 (Rice et al., ibid.) is subjected to partial digestion by the restriction endonuclease SspI, which has cleavage sites at about nucleotides 504, 4130, 7499, and 11954. The desired SspI restriction fragment, which includes a span of nucleotides from about nucleotide 7499 through about nucleotide 504, including nucleotide "0" as indicated in FIG. 6 is isolated, using low melt agarose gel chromatography and elution techniques as described in Sambrook et al., ibid. The desired fragment is then self-ligated using standard ligation technology. The resultant vector, which represents the DNA copy of the packaging vector and is referred to as dPV1, contains the subgenomic promoter, all of the Sindbis virus structural genes, replication and transcription signals at the 5' and 3' ends of the linear viral RNA genome, and a bacteriophage SP6 promoter but does not contain the site thought to be required for packaging in the nsP1 gene or genes that encode functional nsP1, nsP2, nsP3, or nsP4 polypeptides. Thus, the packaging vector can work as a "helper" to provide structural polypeptides "in trans" to enable packaging of recombinant molecules of the present invention.

RNA packaging vector PV1 is produced in a manner similar to the RNA recombinant molecules described in Example 2. Briefly, dPV1 is digested with restriction enzyme SstI, and the linearized DNA is incubated with bacteriophage SP6 RNA polymerase. The resultant RNA is referred to PV1.

Example 4

Production of recombinant virus particle vaccines

A recombinant virus particle vaccine is produced by co-transfecting a host cell with a recombinant molecule and an alphavirus packaging vector, culturing the host cell in an effective medium to produce the vaccine, and recovering the vaccine.

In one experiment, recombinant virus particle vaccine VPV SV2:nP30.1008 is produced by co-transfecting baby hamster kidney (BHK) cells with recombinant molecule SV2:nP30.1008 and packaging vector PV1 using electroporation in a manner similar to that described by Liljestrom et al., ibid. Briefly, BHK cells are grown in 60 mm tissue culture plates to a monolayer confluency of about 90%. The cells are trypsinized, washed once with Minimal Essential Medium (also called MEM; available from Life Technologies Inc., Gaithersburg, Md.) containing 10% fetal calf serum, washed once with ice cold phosphate buffered saline (8 g NaCl, 0.2 g KCl, 1.44 g $Na_2HPO_4$, 0.24 g KH2PO4 per liter of water, the pH of which is adjusted to about pH 7.4; also called PBS) and resuspended in PBS at about $1 \times 10^7$ cells per ml. About 0.5 ml of cells and about 5–10 µg (in about 10–50 microliters [µl]) total of SV2:nP30.1008 and PV1 (at a mole/mole ratio of about 1:1) are mixed in a 0.2 centimeter (cm) cuvette suitable for use in Bio-Rad's Gene Pulser Apparatus (both available from Bio-Rad Laboratories, Richmond, Calif.). The RNA either may be used directly from the in vitro transcription reaction mixture (as described in Example 2 for the recombinant molecule and in Example 3 for the packaging vector) or may be diluted with transcription buffer containing 5 millimolar (mM) dithiothreitol and 1 unit of RNasin per ml. Electroporation is conducted at room temperature by two consecutive pulses at 1.5 kilovolts (KV) and 35 microfarads (µF), using the Gene Pulser Apparatus with the pulse controller unit set at maximum resistance. After electroporation, the cells are diluted about 1:20 in complete BHK cell medium and transferred to tissue culture plates. The cells are then cultured for about 24 to about 36 hours at about 37° C. and about 5% carbon dioxide in about 5 ml of MEM with 10% fetal calf serum.

Plaque forming units (pfu) are quantified by overlaying the monolayers of BHK cells with 2 ml of 1.2% Seakem agarose (available from FMC Corp., Marine Colloids Div., Rockland, Me.) diluted 1:1 (vol/vol) in MEM and 2% fetal calf serum, incubating at about 37° C. for about 24 to about 48 hours, and staining with neutral red or crystal violet.

VPV SV2:nP30.1008 is recovered from the culture using Matrex® Cellufine™ Sulfate Media & Virus Recovery System, available from Amicon Inc., Danvers, Mass.

Example 5

Antigenicity of fusion *Toxoplasma gondii* P30 antigen GST-P30.257

The ability of GST-P30.257, the fusion protein encoded by nucleic acid sequence nGST-nP30.771, to elicit an immune response against toxoplasma infection was determined as follows.

An expression vector containing nGST-nP30.771 was produced by (a) digesting nGST-nP30.771 (produced as described in Example 1G) with XbaI and XhoI; b) inserting the XbaI/XhoI fragment into expression vector Toto2J1 which had also been digested with XbaI and XhoI, to form DNA expression vector dSV:nGST-nP30.771; (c) digesting dSV:nGST-nP30.771 with MluI to form a linear molecule; and (d) transcribing the linear molecule using bacteriophage SP6 RNA polymerase as described in Example 2 to obtain RNA expression vector SV:nGST-nP30.771. Note that Toto2J1 is a Sindbis virus expression vector that contains the SP6 RNA polymerase promoter and the entire Sindbis virus genome through to the NsiI restriction site at nucleotide 11452 (i.e., each of the nonstructural polypeptide genes, the subgenomic promoter, and each of the structural polypeptide genes) ligated to an SspI (nucleotide position 7499)/SstI restriction fragment from TRCAT62 which contains the subgenomic promoter, 14 nucleotides of the 5' untranslated sequence of the subgenomic MRNA, the CAT gene, 62 nucleotides of Sindbis virus 3' untranslated sequence, and the Sindbis virus poly-A sequence.

The GST-P30.257 fusion protein was produced by transfecting SV:nGST-nP30.771 into BHK cells as described above. The transfected cells were then cultured in MEM medium with 10% fetal calf serum for about 24 to about 36 hours at about 37° C. in order to produce GST-P30 recombinant virus. The BHK cells were infected by GST-P30 recombinant virus for about 12 to about 16 hours at 37° C. to produce GST-P30.257. The GST-P30.257 that was expressed from SV:nGST-nP30.771 was specifically recognized by (i.e., selectively bound with high affinity to) polyvalent antiserum produced against native *Toxoplasma gondii* P30 protein, polyvalent antiserum produced against *Toxoplasma gondii* tachyzoite cell lysate, and P30 monoclonal antibodies 1G5 and 5D12 in immunoblot analysis experiments. Rabbit polyvalent antisera produced against native P30 protein or against tachyzoite cell lysates were obtained from L. H. Kasper, Department of Medicine and Microbiology, Section of Neurology, Dartmouth Medical School, Hanover, N.H. P30 monoclonal antibodies 1G5 and 5D12 were obtained from J. S. Remington, Department of Immunology and Infectious Diseases, Research Institute, Palo Alto Medical Foundation, Palo Alto, Calif.

GST-P30.257 was purified by glutathione sepharose 4B chromatography (resin available from Pharmacia Biotech Inc., Piscataway, N.J.) using a technique similar to that described by Smith et al., ibid. The purified protein was used to immunize a rabbit according to the following protocol. About 40 µg of GST-P30.257 was injected into a rabbit on days 0, 21, and 42. Serum was collected from the rabbit at day 56 and found to react with (i.e., bind to) both native *Toxoplasma gondii* P30 antigen and *Toxoplasma gondii* tachyzoite parasites in an immunoblot assay, indicating that GST-P30.257 was capable of eliciting an immune response against toxoplasma infection.

Example 6

Administration of vaccine to mice

Recombinant virus particle vaccine VPV SV2:nP30.1008, produced as described in Example 4, is injected into CD-1 mice using the following protocol. The vaccine is mixed with Hanks' Balanced Salt Solution (HBSS; available from Life Technologies Inc., Gaithersburg, Md.) to give a vaccine formulation of about $1 \times 10^5$ pfu of VPV SV2:nP30.1008 per ml formulation. Each mouse is injected subcutaneously with approximately 0.1 ml of the vaccine formulation at day 0 and at about days 21 to 28. Control CD-1 mice are administered an equivalent amount of native Sindbis virus in HBSS.

The ability of the mice to produce antibodies against *Toxoplasma gondii* parasites is measured using an enzyme-linked immunoassay (ELISA). Purified sonicated parasites are placed in microtiter plates and blocked with 5% Fetal Bovine Serum (FBS). Sera collected from mice are incubated for 2 hr at 37° C. in the parasite-coated microtiter wells and washed with PBS containing 0.4 % of the nonionic detergent Tween 20. Anti-*Toxoplasma gondii* antibodies present in the serum are identified using peroxidase-labeled goat anti-mouse IgG antibodies (available from Cappell Laboratories, Cochranville, Pa.) in a standard ELISA.

The ability of VPV SV2:nP30.1008 to protect the mice from *Toxoplasma gondii* infection is determined as follows. Immunized mice are challenged intraperitoneally with about $5 \times 10^5$ *Toxoplasma gondii* C strain tachyzoites per mouse. Mice are monitored twice a day until signs of lethal toxoplasmosis are evident at which time the mice are euthanized with an overdose of metaphane. After 30 days post challenge, all surviving mice are euthanized with an overdose of metaphane and the number of brain cysts determined by removing the brains from the animals, gently homogenizing the brain tissue in PBS, and counting cysts in 10-µl samples in a hemacytometer. CD-1 mice vaccinated with VPV SV2:nP30.1008 show few if any brain cysts upon infection by *Toxoplasma gondii*, especially as compared to mice vaccinated with Sindbis virus.

Thus, VPV SV2:nP30.1008 is capable of protecting mice from *Toxoplasma gondii* infection. Mice are a suitable model for *Toxoplasma gondii* infection studies since the chronology and outcome of infection in most warm-blooded animals is very similar.

While various embodiments of the present invention have been described in detail, it is apparent that modifications and adaptations of those embodiments will occur to those skilled in the art. It is to be expressly understood, however, that such modifications and adaptations are within the scope of the present invention, as set forth in the following claims:

---

What is claimed is:

1. A method for protecting a Sindbis virus-susceptible animal from disease, comprising:
administering to a Sindbis virus-susceptible animal an effective amount of a recombinant molecule packaged in a Sindbis virus coat, such that said animal is protected from disease, said recombinant molecule including a heterologous nucleic acid sequence operatively linked to a packaging-defective Sindbis virus expression vector, whereby said heterologous nucleic acid sequence encodes a protein or an RNA, and said packaging-defective Sindbis virus expression vector directs transcription of said heterologous nucleic acid sequence.

2. The method of claim 1, wherein said expression vector directs replication of said recombinant molecule.

3. The method of claim 1, wherein said disease is caused by an infectious agent selected from the group consisting of protozoan parasites, helminth parasites and ectoparasites.

4. The method of claim 1, wherein said disease is caused by a parasite selected from the group consisting of protozoan parasites, helminth parasites, ectoparasites, and fungi.

5. The method of claim 1, wherein said disease is caused by an infectious agent selected from the group consisting of the genera Toxoplasma, Dirofilaria, Cryptosporidium, Eimeria, Neospora, Isospora, Plasmoanum, Babesia, Theileria, Hepatozoon, Encephalitozoon, Nosema, Pneumocystis, Cryptococcus, Candida, and Histoplasma.

6. The method of claim 1, wherein the animal is a mammal.

7. The method of claim 1, wherein said animal is selected from the group consisting of humans, pigs, sheep, dogs, cats, cattle, horses, and poultry.

8. The method of claim 1, wherein said recombinant molecule is selected from the group consisting of SV1:nP30.1008, SV1:nP30.924, SV1:nP30.873, SV1:nP30.789, SV1:nP30.771, SV1:nP30.924SS, SV1:nP30.867SS, SV1:nP30.783SS, SV1:nP30.771SS, SV2:nP30.1008, SV2;nP30.924, SV2:nP30.873, SV2:nP30.789, SV2:nP30.711, SV2:nP30.924SS, SV2:nP30.867SS, SV2:nP30.783SS, and SV2:nP30.771SS.

9. The method of claim 1, wherein said heterologous nucleic acid sequence is selected from the group consisting of nP30.1008, nP30.924, nP30.873, nP30.789, nP30.771, nP30.924SS, nP30.867SS, nP30.783SS, and nP30.771SS.

10. The method of claim 1, wherein said heterologous nucleic acid encodes a protein.

11. The method of claim 1, wherein said protein comprises a *Toxoplasma gondii* protein.

12. The method of claim 11, wherein said protein comprises a *Toxoplasma gondii* P30 protein.

13. The method of claim 12, wherein said *Toxoplasma gondii* P30 protein is selected from the group consisting of P30.336, P30.308, P30.291, P30.289, P30.263, P30.261, and P30.257.

14. The method of claim 1, wherein said RNA is an antisense RNA.

15. A method for delivering a packaging-defective recombinant virus particle to a Sindbis virus-susceptible animal, comprising:
administering to a Sindbis virus-susceptible animal an effective amount of a recombinant molecule packaged in a Sindbis virus coat, such that a packaging-defective recombinant virus particle is delivered to said animal, said recombinant molecule including a heterologous nucleic acid sequence operatively linked to a packaging-defective Sindbis virus expression vector, whereby said heterologous nucleic acid sequence encodes a protein or an RNA, and said packaging-defective Sindbis virus expression vector directs transcription of said heterologous nucleic acid sequence.

16. The method of claim 15, wherein said expression vector directs replication of said recombinant molecule.

17. The method of claim 15, wherein said animal is susceptible to disease.

18. The method of claim 15, wherein said disease is caused by an infectious agent selected from the group consisting of protozoan parasites, helminth parasites and ectoparasites.

19. The method of claim 17, wherein said disease is caused by a parasite selected from the group consisting of protozoan parasites, helminth parasites, ectoparasites, and fungi.

20. The method of claim 17, wherein said disease is caused by an infectious agent selected from the group consisting of the genera Toxoplasma, Dirofilaria, Cryptosporidium, Eimeria, Neospora, Isospora, Plasmodium, Babesia, Theileria, Hepatozoon, Encephalitozoon, Nosema, Pneumocystis, Cryptococcus, Candida, and Histoplasma.

21. The method of claim 15, wherein the animal is a mammal.

22. The method of claim 15, wherein said animal is selected from the group consisting of humans, pigs, sheep, dogs, cats, cattle, horses, and poultry.

23. The method of claim 15, wherein said recombinant molecule is selected from the group consisting of SV1:nP30.1008, SV1:nP30.924, SV1:nP30.873, SV1:nP30.789, SV1:nP30.771, SV1:nP30.924SS, SV1:nP30.867SS, SV1:nP30.783SS, SV1:nP30.771SS, SV2:nP30.1008, SV2:nP30.924, SV2:nP30.873, SV2:nP30.789, SV2:nP30.771, SV2:nP30.924SS, SV2:nP30.867SS, SV2:nP30.783SS, and SV2:nP30.771SS.

24. The method of claim 15, wherein said heterologous nucleic acid sequence is selected from the group consisting of nP30.1008, nP30.924, nP30.873, nP30.789, nP30.771, nP30.924SS, nP30.867SS, nP30.783SS, and nP30.771SS.

25. The method of claim 15, wherein said heterologous nucleic acid encodes a protein.

26. The method of claim 15, wherein said protein comprises a *Toxoplasma gondii* protein.

27. The method of claim 26, wherein said protein comprises a *Toxoplasma gondii* P30 protein.

28. The method of claim 27, wherein said *Toxoplasma gondii* P30 protein is selected from the group consisting of P30.336, P30.308, P30.291, P30.289, P30.263, P30.261, and P30.257.

29. The method of claim 15, wherein said RNA is an antisense RNA.

30. The method of claim 1, wherein said recombinant molecule packaged in a Sindbis virus coat forms a recombinant virus particle, wherein said particle is selected from the group consisting of VPV SV1:nP30.1008, VPV SV1:nP30.924, VPV SV1:nP30.873, VPV SV1:nP30.789, VPV SV1:nP30.771, VPV SV1:nP30.924SS, VPV SV1:nP30.867SS, VPV SV1:nP30.783SS, VPV SV1:nP30.771SS, VPV SV2:nP30.1008, VPV SV2:nP30.924, VPV SV2:nP30.873, VPV SV2:nP30.789, VPV SV2:nP30.771, VPV SV2:nP30.924SS, VPV SV2:nP30.867SS, VPV SV2:nP30.783SS, and VPV SV2:nP30.771SS.

31. The method of claim 1, wherein said Sindbis virus expression vector encodes Sindbis virus nonstructural polypeptides nsP1, nsP2, nsP3, and nsP4.

32. The method of claim 1, wherein said Sindbis virus expression vector comprises an alphavirus subgenomic promoter operatively linked to said heterologous nucleic acid sequence.

33. The method of claim 32, wherein said subgenomic promoter is selected from the group consisting of Sindbis virus subgenomic promoters, Semliki Forest virus subgenomic promoters, Ross River virus subgenomic promoters, and hybrids thereof.

34. The method of claim 33, wherein said subgenomic promoter is a Sindbis virus subgenomic promoter.

35. The method of claim 1, wherein said nucleic acid sequence is joined to at least one additional nucleic acid sequence which encodes at least one additional protein to form a nucleic acid fusion fragment, wherein said fusion fragment encodes a fusion protein comprising at least two proteins.

36. The method of claim 1, wherein said recombinant molecule further comprises an immunopotentiator.

37. The method of claim 1, wherein said recombinant molecule is administered by injection.

38. The method of claim 1, wherein said recombinant molecule is administered by oral application.

39. The method of claim 1, wherein said recombinant molecule is administered by nasal application.

40. The method of claim 1, wherein said recombinant is administered by topical application.

41. The method of claim 1, wherein said disease is caused by fungi.

42. The method of claim 1, wherein said disease is caused by bacteria.

43. The method of claim 1, wherein said disease is caused by a virus.

44. The method of claim 15, wherein said recombinant molecule packaged in a Sindbis virus coat forms a recombinant virus particle, wherein said particle is selected from the group consisting of VPV SV1:nP30.1008, VPV SV1:nP30.924, VPV SV1:nP30.873, VPV SV1:nP30.789, VPV SV1:nP30.771, VPV SV1:nP30.924SS, VPV SV1:nP30.867SS, VPV SV1:nP30.783SS, VPV SV1:nP30.771SS, VPV SV2:nP30.1008, VPV SV2:nP30.924, VPV SV2:nP30.873, VPV SV2:nP30.789, VPV SV2:nP30.771, VPV SV2:nP30.924SS, VPV SV2:nP30.867SS, VPV SV2:nP30.783SS, and VPV SV2:nP30.771SS.

45. The method of claim 15, wherein said Sindbis virus expression vector encodes Sindbis virus nonstructural polypeptides nsP1, nsP2, nsP3, nsP4.

46. The method of claim 15, wherein said Sindbis virus expression vector comprises an alphavirus subgenomic promoter operatively linked to said heterologous nucleic acid sequence.

47. The method of claim 46, wherein said subgenomic promoter is selected from the group consisting of Sindbis virus subgenomic promoters, Semliki Forest virus subgenomic promoters, Ross River virus subgenomic promoters, and hybrids thereof.

48. The method of claim 47, wherein said subgenomic promoter is a Sindbis virus subgenomic promoter.

49. The method of claim 15, wherein said nucleic acid sequence is joined to at least one additional nucleic acid sequence which encodes at least one additional protein to form a nucleic acid fusion fragment, wherein said fusion fragment encodes a fusion protein comprising at least two proteins.

50. The method of claim 15, wherein said recombinant molecule further comprises an immunopotentiator.

51. The method of claim 15, wherein said recombinant molecule is administered by injection.

52. The method of claim 15, wherein said recombinant molecule is administered by oral application.

53. The method of claim 15, wherein said recombinant molecule is administered by nasal application.

54. The method of claim 15, wherein said recombinant is administered by topical application.

55. The method of claim 15, wherein said disease is caused by fungi.

56. The method of claim 15, wherein said disease is caused by bacteria.

57. The method of claim 15, wherein said disease is caused by a virus.

* * * * *